United States Patent
Li et al.

(10) Patent No.: US 7,419,538 B2
(45) Date of Patent: Sep. 2, 2008

(54) HIGHLY ANTI-CORROSIVE METAL PIGMENTS

(75) Inventors: Bangyin Li, Fukushima Pref. (JP); Nobuaki Nakamura, Fukushima Pref. (JP); Katsuhisa Nitta, Fukushima-ken (JP)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/485,483

(22) PCT Filed: Jul. 1, 2002

(86) PCT No.: PCT/EP02/07221

§ 371 (c)(1),
(2), (4) Date: Feb. 2, 2004

(87) PCT Pub. No.: WO03/014228

PCT Pub. Date: Feb. 20, 2003

(65) Prior Publication Data

US 2004/0194663 A1 Oct. 7, 2004

(30) Foreign Application Priority Data

Aug. 2, 2001 (JP) ............................. 2001-234461

(51) Int. Cl.
*C09C 1/64* (2006.01)
*C09C 1/66* (2006.01)

(52) U.S. Cl. .................. 106/403; 106/404; 106/415; 106/416; 106/14.21

(58) Field of Classification Search .................. 106/403, 106/404, 415, 416, 14.21
See application file for complete search history.

(56) References Cited

U.S. PATENT DOCUMENTS

| 4,808,231 | A | * | 2/1989 | Kondis ....................... 106/404 |
| 5,135,812 | A | | 8/1992 | Phillips et al. |
| 5,352,286 | A | * | 10/1994 | Schmid et al. .............. 106/404 |
| 5,474,605 | A | * | 12/1995 | Schmid et al. .............. 106/404 |
| 5,607,504 | A | * | 3/1997 | Schmid et al. .............. 106/403 |
| 5,624,486 | A | * | 4/1997 | Schmid et al. .............. 106/404 |
| 5,733,364 | A | | 3/1998 | Schmid et al. |

(Continued)

FOREIGN PATENT DOCUMENTS

DE 19836810 2/2000

(Continued)

OTHER PUBLICATIONS

Patent Abstracts of Japan ; Publication No. 2003-041150, published Feb. 13, 2003, Merck Ltd.

(Continued)

*Primary Examiner*—C. Melissa Koslow
(74) *Attorney, Agent, or Firm*—Millen, White, Zelano, Branigan, P.C.

(57) ABSTRACT

Highly anti-corrosive thin-platelet like metal pigments having high corrosion resistance and good dispersibility characterized in that the inherent metallic luster of the thin-platelet like metal substrates is maintained without demanding the original surface smoothness are provided. The highly anti-corrosive thin-platelet like metal pigments comprising, on the surface of thin-platelet like metal substrates treated with phosphoric acid compounds and/or boric acid compounds, one or more coated layers containing one or more hydrated metal oxides of one or more metals selected from the group consisting of silicon, aluminum, zirconium, titanium and tin.

25 Claims, 5 Drawing Sheets

(Test condition, 75 °C, pH 1.8 HCl Solution: 100g, sample:1g)

U.S. PATENT DOCUMENTS

| | | |
|---|---|---|
| 5,766,335 A | 6/1998 | Bujard et al. |
| 6,150,022 A | 11/2000 | Coulter et al. |
| 6,157,489 A | 12/2000 | Bradley, Jr. et al. |
| 6,238,472 B1 | 5/2001 | Andes et al. |
| 6,284,032 B2 | 9/2001 | Andes et al. |
| 6,340,723 B1 | 1/2002 | Nitta et al. |
| 6,369,147 B1 | 4/2002 | Polonka et al. |
| 6,383,638 B1 | 5/2002 | Coulter et al. |
| 6,387,498 B1 | 5/2002 | Coulter et al. |
| 6,776,835 B2 | 8/2004 | Andes et al. |
| 2002/0137819 A1 | 9/2002 | Polonka et al. |
| 2004/0166316 A1 | 8/2004 | Noguchi |
| 2004/0194663 A1 | 10/2004 | Li et al. |

FOREIGN PATENT DOCUMENTS

| | | |
|---|---|---|
| EP | 1090963 | 4/2001 |
| JP | 2002-088274 | 3/2002 |
| WO | WO 03/014228 A1 | 2/2003 |

OTHER PUBLICATIONS

Patent Abstracts of Japan, Publication No. 08-209024, published Aug. 13, 1996, BASF AG.

* cited by examiner

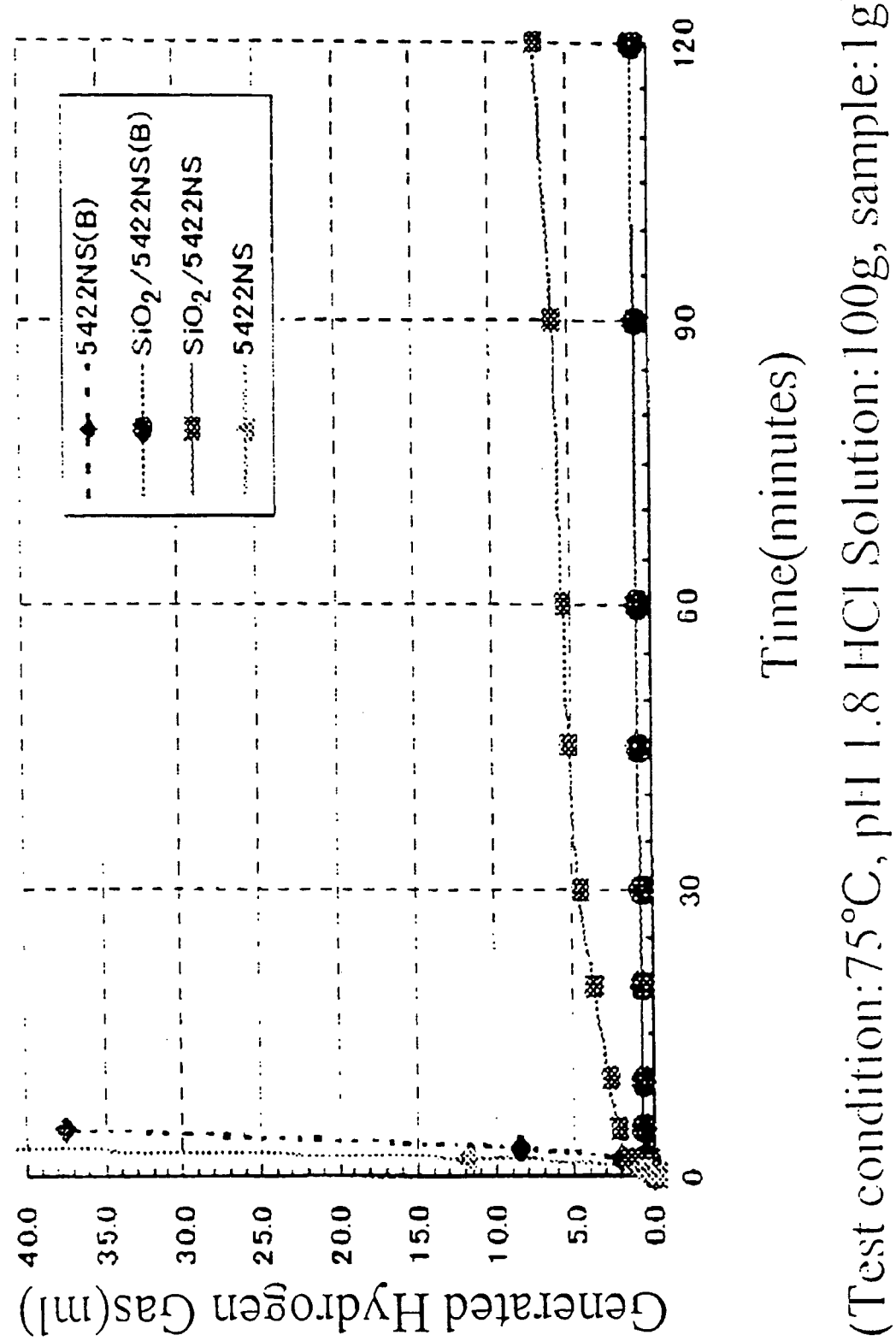

HIGHLY ANTI-CORROSIVE METAL PIGMENTS

Highly anti-corrosive thin-platelet like pigment, the preparing method of the same and the interference colored pigments having metallic luster of which base is the same.

FIELD OF THE INVENTION

The present invention relates to novel highly anti-corrosive thin-platelet like metal pigment the preparing method of the same, interference colored pigments having a metallic luster of which base is the same, and use of the same, etc.

BACKGROUND OF THE INVENTION

Commercially available pearl-luster pigments which use thin-platelet like mica substrates coated with highly refractive metal oxides (called "interference color layer" hereinafter) such as titanium oxide etc. to exhibit color through interference are well known. However, since the mica is semi-transparent, their reflectivity is low; therefore, expression of interference color by action of interference is not fully achieved. Thus there appear the interference colored pigments where metal which is opaque and has a high optical reflectance is used as thin-platelet like substrate and an interference color layer (such as titanium oxide, etc) is coated on its surface (forex, JP (A) Hei. 1-110568, JP (A) Hei. 2-669, etc). In these interference colored pigments, the interference color is layer indirectly coated by means of the so-called sol-gel method avoiding an aqueous water treatment, since thin-plate like metal substrate have a disadvantage that they can easily react with water and easily be oxidized.

Further, goniochromatic pigments (multi-chromatic interference colored pigments) has also been known, wherein on the surface of thin-platelet like metal substrate, the first coating layer is formed using hydrated silicon oxide (as an example of a substance having a low refractive index) by the so-called Sol-Gel method, then other metal oxide having a high refractive index is coated thereon by vapor phase reaction and repeated too give a lure charge (color travel effect) due to changes in viewing angle (ex. JP (A) Hei. 8-209024, JP (A) Hei. 8-302237, JP (A) Hei. 9-124971).

Moreover, in order to obtain a highly anti-corrosive layer (passivation layer), it has been known that there were a product which is treated with phosphoric acids, etc, (e.g. DE 19836810.0 etc.), a product which is treated with organic phosphoric acids (e.g. JP (A) Hei. 3-74472, JP (PCT) 2001-502375, etc.), a product which is treated only with silica (e.g. JP (A) Hei. 8-209025; U.S. Pat. No. 2,885,366 and U.S. Pat. No. 3,954,496; etc.), a product where a treatment with containing volatile phosphorus compounds and volatile nitrogen containing organosilicon compounds by the vapor phase method is carried out (JP (A) Hei. 7-292279), and so forth.

However, in these conventional methods there is the disadvantage that expensive raw materials have to be used or that the inherent smoothness of the surface of thin-platelet like metal substrate is not maintained but is deteriorated or the dispensability of particles is insufficient resulting in irregular reflection whereby the reflected light on the surface of thin-platelet metal can not be adequately utilized. Accordingly, even when the upper interference color layer is further coated thereon it is not possible to sufficiently achieve the expression of the interference color.

In particular, because the anti-corrosive property to acidic aqueous solution is insufficient, it is not possible to carry out the treatment in an aqueous system where the cost is low and the operation is easy in terms of facilities thereon. Namely, it is not possible to adopt a method in which hydrated metal oxides obtained by neutral hydrolysis using water-soluble metal salts and alkali or by a thermal hydrolysis of water-soluble metal salts in an aqueous system, are coated, filtered, dried and, if desired, calcined (this will be defined as a wet-process method" as a whole including the description in the claims). In addition, as mentioned above, smoothness and denseness of the surface to which the anti-corrosive layer is coated are not sufficient and, further the affinity between the hydrated metal oxide layers constituting such an anti-corrosive layer and the hydrated metal oxide layer constituting the interference color layers coated thereon is not sufficient, whereby it is impossible to achieve a homogenity and denseness of the hydrated metal oxide layer constituting the interference color layer; whereby, interference color having a high coloration can not be exhibited.

In other cases such as the adoption of vapor phase method (e.g. in JP (A) Hei. 8-209024, JP (A) Hei. 8-302237, JP (A) Hei. 9-124971, etc.), there are disadvantage that production facilities are expensive, volatilizing temperature of the method used in restricted (JP(A)7-292279), whereby in general more strict reaction control is required than an aqueous phase reaction, etc. Thus there has been a demand for utilizing the above-mentioned conventional method which is so-called wet-process method.

SUMMARY OF THE INVENTION

[Object of the Invention]

Thus, an object of the present invention is to provide highly anti-corrosive thin-platelet like metal pigments having high corrosion resistance and good dispersibility, wherein the inherent metallic luster of thin-platelet like metal substrate is maintained without damaging the original surface smoothness of thin-platelet like metal substrate. Another object of the present invention is to provide an interference colored pigment having a metallic luster, a high interference coloration and a color travel effect wherein it is possible to adopt the so-called wet process method for coating hydrated metal oxides onto the surface of a highly anti-corrosive thin-platelet like metal pigment even when in an acidic aqueous solution.

[Means for Achieving the Object of the Invention]

In order to solve the above-mentioned problems, the inventors of the present invention have carried out eager investigations and found that highly anti-corrosive metal pigment having coated layer containing hydrated metal oxide on the surface of thin-platelet like metal substrate treated with phosphoric acids compounds and/or boric acid compounds is able to solve the above-mentioned problems whereupon the present invention has been accomplished.

Thus, the present invention relates to highly anti-corrosive thin-platelet like metal pigments comprising, on the surface of thin-platelet like metal substrates treated with phosphoric acid compounds and/or boric acid compounds, one or more coatings containing one or more hydrated metal oxides of one or more metals selected from the group consisting of silicon, aluminum, tin, zirconium and titanium.

The invention also relates to the above-mentioned highly anti-corrosive thin-platelet like metal pigments, wherein the thin-platelet like metal substrates are metallic pigment having luster.

The present invention further relates to the above-mentioned highly anti-corrosive thin-platelet like metal pigments, wherein the metallic pigments having luster is any one of aluminium flakes, titanium flakes, gold flakes, silver flakes, copper-zinc alloy flakes, stainless steel flakes or bronze flakes.

The present invention also relates to the above-mentioned highly anti-corrosive thin-platelet like metal pigments, wherein the hydrated metal oxides are hydrated silicon oxides.

The present invention further relates to the above-mentioned highly anti-corrosive thin-platelet like metal pigments, wherein the hydrated metal oxides are prepared by the sol-gel method.

The present invention also relates to the above-mentioned highly anti-corrosive thin-platelet like metal pigments, wherein the sol-gel method is performed by hydrolysis of metal alkoxide.

The present invention further relates to the above-mentioned highly anti-corrosive thin-platelet like metal pigments, wherein the hydrolysis of the metal alkoxide is performed by using a basic catalyst.

The present invention also relates to the above-mentioned highly anti-corrosive thin-platelet like metal pigments, wherein the amount of phosphoric acids compounds and/or boric acids compounds used, is corresponding to 0.0001-0.1 g as $P_2O_5$ and/or $B_2O_3$ per unit surface area ($m^2$) of thin-platelet like metal substrates and the amount of metal compounds used for preparing a hydrated metal oxide coated layer, is corresponding to 0.01-1.0 g as metal oxide of $SiO_2$, $Al_2O_3$, $ZrO_2$, $TiO_2$ and $SnO_2$ per unit surface area ($m^2$) of thin-platelet like metal substrates.

The present invention further relates to the preparing method of highly anti-corrosive thin-platelet like metal pigments, wherein, dispersing thin-platelet like metal substrate in the polar organic solvent, and the method contains a process of 1) adding phosphoric compounds and/or boric acids compounds thereto, stirring it, and accordingly treatiry its substrate, simultaneously or subsequently.

2) preparing coated layer of a hydrated metal oxide on the surface of said substrates by the sol-gel method.

The present invention also relates to the above-mentioned preparing method, wherein the sol-gel method is performed by hydrolysis of metal alkoxide solution that is dissolved in a polar organic solvent.

The present invention further relates to the above-mentioned preparing methods, wherein the metal composing the layer of metal oxide coating are one or more metals selected from the group consisting of silicon, aluminum, zirconium, titanium and tin.

The present invention also relates to the above-mentioned preparing method characterized in the metal alkoxide solution is added after adding water and a catalyst.

The present invention further relates to the above-mentioned preparing method, wherein the metal alkoxide solution and the aqueous solution containing a catalyst.

The present invention also relates to the above-mentioned preparing method, wherein the aqueous solution containing catalyst is added after addition of the metal alkoxide solution.

The present invention further relates to the above-mentioned preparing method, wherein the catalyst is a basic catalyst.

The present invention also relates to the interference colored pigments having metallic luster, wherein the surface of the highly anti-corrosive thin-platelet like metal pigment further coated with a secondary hydrated metal oxide layers comprising one or more layers.

The present invention further relates to the above-mentioned interference colored pigments having metallic luster, wherein the secondary of coated layer hydrated metal oxides is prepared by wet process method, a chemical vapor deposition process method or a physical vapor deposition process method.

The present invention also relates to the above-mentioned interference colored pigments having metallic luster, wherein the secondary coated layer of hydrated metal oxides is prepared by wet process method.

The present invention further relates to the above-mentioned interference colored pigments having metallic luster, wherein the secondary coated layer of hydrated metal oxides is the coated layer containing one or more hydrated metal oxides of one or more metals selected from the group consisting of titanium, aluminum, zirconium, tin, zinc, iron, chromium, cobalt, silicon and boron.

The present invention also relates to the above-mentioned interference colored pigments having metallic luster, wherein the secondary coated layers of hydrated metal oxides are multi-coated layers having different hydrated metal oxides.

The present invention further relates to the above-mentioned interference colored pigments having metallic luster, wherein the secondary coated layer of hydrated metal oxides are alternatively multi-coated layer of metal oxide or hydrates having a high refractive index and a low refractive index.

The present invention also relates to the use of the above-mentioned highly anti-corrosive thin-platelet like metal pigment or the above-mentioned interference colored pigments having metallic luster in paints, powder coatings, its painting layers, inks, security printing inks, plastics, pellets, moldings, and cosmetics.

The present invention further relates to a composition comprising the above-mentioned highly anti-corrosive thin-platelet like metal pigments or the above-mentioned interference colored pigments having a metallic luster in combination with one or more pigments selected from the group consisting of organic pigments, inorganic pigments, effect pigments, fillers, and functional pigments.

The highly anti-corrosive thin-platelet like metal pigments of the present invention, have a good anti-corrosive property without deteriorating the smoothness of the surface of metal substrate, and particularly since hydrogen gas is rarely generated even in an acidic aqueous solution, it is now possible to carry out a coating of hydrated metal oxide layer by wet process method, which has been said to be unsuitable to a metal substrate.

As for the highly anti-corrosive thin-platelet like pigments, although the mechanism for the changes in properties resulted by the combination of the treatment with phosphoric acids compounds and/or boric acids compounds and the preparation of a coated layer containing hydrated metal oxides is not necessarily clear; however, the detained highly anti-corrosive thin-platelet like metal pigments can render not only anti-corrosive property by passivation, but also denseness and smoothness of the surface which have not been available in conventional anti-corrosive treatment, and further achieve a good dispersibility of the obtained pigments due to the above-mentioned combination. Consequently, when the highly anti-corrosive thin-platelet like metal pigments according to the present invention are used as substrates of interference colored pigments, it is possible to obtain dense and homogeneous coating and interference colored pigments having metallic luster with good dispersibility, since the pigments have a good affinity with the hydrated metal oxide layer to be coated due to their surface of denseness. The pigments obtained as a result thereof have both inherent laboring of the metal due to the high reflecturance from the surface of the thin-platelet substrate and good interference colors due to interference if the coated hydrated metal oxides layer, resulting in change of hue (color travel effect) by changing the view angle. Thus it is a novel interference color pigment having a metallic luster, wherein its coloration (chromaticity) surprisingly improved.

BRIEF DESCRIPTION OF THE DRAWINGS

FIG. 5 shows a comparison of the amount of hydrogen gas in the case of use of 5422NS was used among the untreated 5422NS, 5422NS(B), $SiO_2$/5422NS(B) and $SiO_2$/5422NS.

BEST MODES FOR CARRYING OUT THE INVENTION

Figure 1:
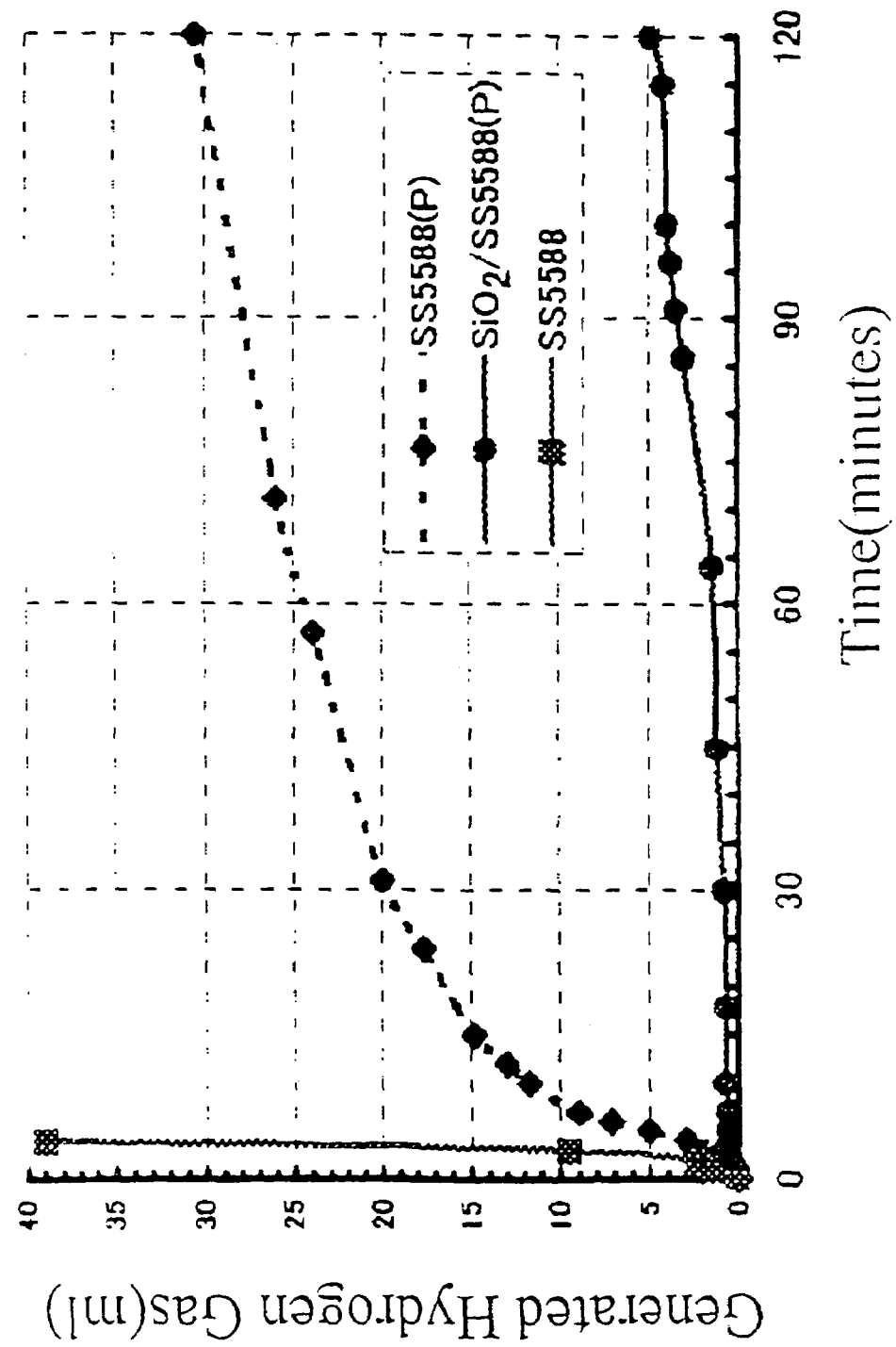
FIG. 1 shows a comparison of the amount of hydrogen gas in the case of use of SS5588 was used among the untreated SS5588, SS5588(P) and $SiO_2$/SS5588(P).

Hereinafter, the present invention will be explained in more detail together with the preparing method.

The thin-platelet like metal substrates used in the present invention are so-called metallic pigments which contain thin-platelet like metals and metal alloys.

The thin-platelet like metal substrates used in the present invention preferably have an average particle diameter of 2-100 μm and an average thickness of 0.05-5 μm, more preferably they have an average particle diameter of 5-50 μm and an average thickness of 0.1-2 μm, and even more preferably they have an average particle diameter of 5-30 μm and an average thickness of 0.1-2 μm.

Specific examples of flakes include aluminum flakes, titanium flakes, gold flakes, silver flakes, copper-zinc alloy flakes, iron flakes, bronze flakes, stainless steel flakes, aluminum bronze flakes, flakes of various aluminum alloys, flakes of various titanium alloys, etc. Preferred flakes include aluminum flakes, titanium flakes, gold flakes, silver flakes, copper-zinc alloy flakes, stainless steel flakes, bronze flakes, etc.; even more preferred flakes include the widely sold brilliant metallic pigments such as aluminum flakes (from e.g. Silberline; Showa Aluminum Co., Ltd.; Toyo Aluminum Co., Ltd.; Asahi Kasei Metals Co., Ltd.; Eckart-Werke; etc.), titanium flakes, stainless steel flakes, etc. of which there is a stable supply commercially available; and most preferred are aluminum flakes.

Among these, thin-platelet like metal substrates commercially available in various states may be used, such as those substrate flakes that have already been suspended in an organic solvent to prevent oxidative corrosion caused by the moisture contained in the air (e.g., pigment pastes suspended in mineral spirit, etc.), those substrates that, for the purpose of leafing or for improving dispersibility, have been treated with different types of surface treatment agents and have been suspended in an organic solvent and those substrate on whose surface an oxidation protection film (passivation film, i.e. surface oxidized thin-film layer) has been applied beforehand. Regarding the object of the present invention, its effect is brought out particularly by metal flakes having high corrosiveness, as long as the surface is largely free from oxidation; hence the use thereof is preferred.

For example, those substrates with high corrosiveness such as aluminum flakes which are available in the market at the state of suspension in an organic solvent before being handled and those substrates which have been treated with different surface treatment agents and have been suspended in an organic solvent are particularly recommended for use in the present invention.

When using thin-platelet like metal substrates which have been subjected beforehand to an anti-corrosive (passivation) treatment and those alloy substrates, there is no need to perform the treatment based on the present invention simply to confer corrosion resistance; however, apart from improving the durability of the corrosion protection, the anti-corrosive layer according to the present invention, different from the above-mentioned anti-corrosive treatments, is also effective for forming a smooth, homogeneous and dense and dense layer of hydrated metal oxides thereafter.

Next, a suspension is prepared with a polar organic solvent in which these thin-platelet like metal substrates are dispersed. According to the present invention, the suspension of a polar organic solvent is defined as the material that can be prepared as follows:

(1) thin-platelet like metal substrates suspended in an organic solvent are suspended, as they are, in a polar organic solvent to obtain a suspension with the desired concentration;

(2) thin-platelet like metal substrates as solid parts (the flakes are not completely dried so that some adhering solvent remains to prevent direct contact with air and moisture) are retrieved beforehand by filtration and centrifugal separation of the organic solvent, and are then suspended in a polar organic solvent to obtain a suspension with the desired concentration;

(3) if the thin-platelet like metal substrates have already been treated with a surface treatment agent, the surface treatment agent is washed and removed using a polar organic solvent, and after filtration, the substrates are again suspended using a polar organic solvent to obtain a suspension with the desired concentration;

(4) if the thin-platelet like metal substrates are available in the market as the state of the powder which has been subjected to a passivation treatment, they are suspended, as they are, in a polar organic solvent to obtain a suspension with the desired concentration.

Examples of polar organic solvents used in the present invention include ketones such as acetone, methyl ethyl ketone (MEK), methyl isobutyl ketone (MIBK), etc.; alcohols with an alkyl group having 1-10 carbon atoms; tetrahydrofuran (THF); dimethylformamide (DMF); dimethylsulfoxide (DMSO); dioxanes; polyols and cellosolve solvents. Among these, alcohols which are in the liquid state at normal temperatures may be selected; examples of which include e.g. methanol, ethanol, isopropylalcohol, butanol, isobutanol, pentanol, hexanol, heptanol, octanol, isooctanol, nonanol, decanol and isomers thereof. Examples of preferred alcohols include ethanol, isopropylalcohol, butanol, isobutanol because they are inexpensive and easy to handle at normal temperature. Especially isopropylalcohol and ethanol etc. are used because of their low volatility and low cost. Moreover, these solutions may also be appropriately mixed. Further, if metal alkoxide is used for forming the hydrated metal oxide layer (defined as the "second stage coating" in the present specification), alcohols having a high compatibility with metal alkoxides are selected for the polar organic solvent used in the present invention. Naturally, an appropriate selection needs to be made also in consideration of the compatibility with the phosphoric acid compounds and boric acid compounds used. From an economic point of view it is desirable to use the same polar organic solvent for the treatment with phosphoric acid compounds and/or boric acid compounds (defined as the "first stage treatment" in the present requirement) and for the second stage coating reaction; however, it is also possible to use different solvents for the respective treatment and coating stages when taking into consideration reaction efficacy and the compatibility with the reactants used at the respective reaction stages. Further, the polar organic solvent used for removing the surface treatment agents described in (3) above is appropriately selected in consideration of its compatibility with the surface treatment agent.

The concentration of the suspension of a polar solvent in which the thin-metallic like metal substrates have been suspended can be appropriately changed according to the density of the those metal substrates used, the performance of the agitator and the viscosity of the solvent.

The treatment with phosphoric acid compounds and/or boric acid compounds in the present invention corresponds to a pretreatment for forming a hydrated metal oxide layer which is treated simultaneously or subsequently; i.e., by combining this treatment with the second stage coating the object of the present invention is achieved.

The highly anti-corrosive thin-platelet like metal pigments obtained are one part of the present invention (claims 1-8) characterized in that good anti-corrosive properties, good brilliance and good dispersibility with little particle agglomeration are achieved.

In the present invention, the first stage treatment or the second stage coating cannot, each on its own, achieve the objects of the present invention, i.e. corrosion resistance and the homogeneous and dense hydrated metal oxides obtained by the wet process method performed thereafter. Further, even if the order is inverted, and the first stage treatment is performed after the second stage coating, it is not possible to obtain an effect superior to that obtained by the second stage coating on its own.

Consequently, it is important that the hydrated metal oxide layer is formed on a surface treated with phosphoric acid compounds and/or boric acid compounds, and as long as this constitution is achieved it is also possible to perform the first stage treatment and the second stage coating simultaneously or subsequently; however, is preferred to perform first the first stage treatment and then the second stage coating to assure that said constitution is achieved.

Hereinafter, the first stage treatment will be explained.

The treatment with phosphoric acid compounds and/or boric acid compounds is performed by adding the phosphoric acid compounds and/or boric acid compounds to the suspension of a polar organic solvent in which thin-platelet like metal substrates have been suspended.

Taking into consideration good anti-corrosive property, dispersibility and economic factors, the amount of phosphoric acid compounds and/or boric acid compounds used, preferably is an amount corresponding to 0.0001-0.1 gas $P_2O_5$ and/or $B_2O_3$ per unit surface area ($m^2$) of thin-platelet like metal substrates, even more preferably is an amount corresponding to 0.0002-0.08 g and still more preferably is an amount corresponding to 0.0005-0.05 g. Thus, the amount used for this treatment is naturally determined in view of the unit surface area of the thin-platelet like metal substrates; i.e. a small amount is used when the particle diameter is big, while a large amount is required if the particle diameter is small.

When using phosphoric acid compounds and boric acid compounds in an aqueous solution, it is preferred to determine the amount of water so as not to become excessive while taking into consideration the amount used (consumed) in subsequent processes and so that the surface roughness of the raw material of the thin-platelet like metal substrates does not increase. Further, it is also possible to use these solvents of phosphoric acid compounds and boric acid compounds with the water mentioned before dissolved together as one solvent with the polar organic solvents subsequently used for preparing the suspension of thin-platelet like metal substrates. In any case, the polar organic solvent used is appropriately selected while taking into consideration its affinity and compatibility the thin-platelet like metal substrates with phosphoric acid compounds and boric acid compounds.

Examples of phosphoric acid compounds used in the present invention include phosphoric acid, orthophosphoric acid, metaphosphoric acid, tripolyphosporic acid, hypophosphorous acid, phosphorous acid, various polyphosphates thereof, various phosphates thereof having at least one OH group, organic acidic phosphoric acid esters (e.g., methyl acid phosphoric acid, butyl acid phosphoric acid, dibutyl acid phosphoric acid, monobutyl acid phosphoric acid, 2-ethylhexyl acid phosphoric acid, bis-2-ethylhexyl acid phosphoric acid, isodecyl acid phosphoric acid, diisodecyl acid phosphoric acid, etc.), organic acidic phosphorous acid esters (e.g., dibuthyl hydrogen phosphite etc.), 2-methacryloyloxyethyl acid phosphoric acid, hydroxyethanediphosphonic acid $\{CH_3C(OH)(PO_3H_2)_2\}$, phosphoric acid bis[2-(N-propyl perfluorooctylsulfonyl amino)ethyl]ester, perfluoroalkyl-ethyl phosphoric acid ester (e.g., $(RfCH_2CH_2O)P(O)(OH)_2$, $(RfCH_2CH_2O)_2P(O)(OH)$, characterized in that Rf represents a perfluoroalkyl group of $CF_3(CF_2)_{6-17}$). The terms "acidic" and "acid" in the above-mentioned phosphoric acid compounds mean that such as phosphoric acid compounds has at least one OH group. Further, by selecting an appropriate organic ester group as bonded group of the phosphoric acid compounds, it is possible to increase the affinity with the polar organic solvent used in the subsequent reaction.

Examples of boric acid compounds used in the present invention include boric acid, boric acid ammonium, metaboric acid, metaboric acid lithium, metaboric acid ammonium, hypoboric acid, hypoboric acid ammonium, etc.

The treatment of the highly anti-corrosive thin-platelet like metal pigments of the present invention can be performed by phosphoric acid compounds, by boric acid compounds or by both phosphoric acid and boric acid compounds, etc., as long as the object of the present invention is achieved.

After the treatment has been completed, the suspension can be used as it is or the solid parts can be retrieved by filtration to perform the subsequent second stage coating reaction.

Hereinafter, the second stage coating reaction will be explained.

Considering that metal substrates are used, it is preferred to perform the coating of the hydrated metal oxides by a sol-gel method; among these, a method using metal alkoxide as metal compound to be hydrolyzed is preferred.

The suspension obtained by the first stage treatment reaction can be used as it is, or the solid parts retrieved by filtration can again be dispersed in a polar organic solvent, which may be identical to or different from the one of the first stage treatment reaction, to prepare a suspension. The second stage coating, requiring the presence of a catalyst, is formed by adding metal compounds and a predetermined amount of water necessary for hydrolysis. It is possible to use an acidic catalyst for the hydrolysis; however, for forming a homogeneous and dense treatment coated layer, ammonium compounds and/or amino-compounds are preferred. The use of a basic catalyst is characteristic of the present invention.

Taking into consideration corrosion resistance and economic factors, the amount of metal alkoxide or other metal compounds used according to the present invention, calculated as $SiO_2$, $Al_2O_3$, $ZrO_2$, $TiO_2$ and $SnO_2$, preferably is an amount corresponding to 0.01-1.0 g per unit surface area ($m^2$) of thin-platelet like metal substrates, even more preferably is an amount corresponding to 0.02-0.8 g and still more preferably is an amount corresponding to 0.05-0.5 g.

Examples of metals used for the hydrated metal oxides for forming the highly anti-corrosive thin-platelet like metal pigments according to the present invention include silicon, aluminum, zirconium, titanium and tin, which as hydrated metal oxides are transparent. These hydrated metal oxides can be oxides of one type of metal or composite oxides of two or more types of metal; however, taking into consideration their high transparency, their low index of refraction and the low cost of the raw material, hydrated silicon oxides are particularly preferred.

Moreover, it is also possible to form multi-layers of hydrated metal oxide layers comprising one or more kinds of these hydrated metal oxides. Examples of raw materials used at this stage include metal alkoxides and organic acid salts.

Specific examples of silicon alkoxides used in the present invention include e.g. tetramethoxy silicate, tetraethoxy silicate, tetrapropoxy silicate, tetraisopropoxy silicate, tetrabutoxy silicate, tetrapentoxy silicate, tetrahexoxy silicate, so-called silane coupling agents (e.g., alkoxy silicate having an alkyl group, alkoxy silicate having an aminoalkyl group, alkoxy silicate having a glycidylalkyl group, etc.). Each of them may be used either solely or in combination. When using a silane coupling agent, a desired surface modification can be designed.

Specific examples of aluminum alkoxides include e.g. aluminum triethoxide, aluminum tri-iso-propoxide, aluminum tri-sec-butoxide, aluminum ethylacetate di-iso-propoxide, etc.

Specific examples of zirconium alkoxides include e.g. zirconium tetraethoxide, zirconium tetra-n-propoxide, zirconium tetra-iso-propoxide, zirconium tetra-n-butoxide, etc.

Specific examples of titanium alkoxides include titanium tetraethoxide, titanium tetra-n-propoxide, titanium tetra-iso-propoxide, titanium tetra-n-butoxide, etc.

Specific examples of tin alkoxides include e.g. tin tetraethoxide, tin tetra-iso-propoxide, etc.

As polar organic solvents for the second stage coating reaction, it is preferred to use alcohols constituting metal alkoxides.

The ammonium compounds and/or amino compounds that can be used as basic catalysts in the second stage coating reaction, in addition to serving as catalyst for hydrolyzing the metal alkoxide by the sol-gel method, are also useful for forming a homogeneous and dense coated layer of hydrated metal oxides.

Specific examples of ammonium compounds used in the present invention include e.g. ammonia, ammonium carbonate, ammonium phosphoric acid, ammonium acetate, ammonium oxalate, ureas, etc.; and specific examples of amino compounds include e.g. γ-aminopropyl triethoxy silicate, triethanolamine, diethanolamine, and their salts. Among these, γ-aminopropyl triethoxy silicates etc. combine in the same molecule the two functions of the above-mentioned silicon alkoxides and the amino component, hence they are appropriately selected to obtain the desired properties.

From the point of view of reaction rate, anti-corrosive property and the amount of hydrated metal oxides to be coated etc., the amount of these basic catalysts, i.e. the ammonium and/or amino compounds, preferably is an amount corresponding to 0.01-100 mol, and especially preferably an amount corresponding to 0.1-30 mol per 1 mol of metal alkoxide compounds.

Any of the following methods may be adopted for adding water in said sol-gel method:

(1) adding the amount of water necessary for hydrolysis to the suspension obtained by the first stage treatment reaction before adding a solution of metal alkoxides, (2) adding water and metal alkoxide separately and at the same time to the suspension obtained by the first stage treatment reaction, and (3) adding metal alkoxide to the suspension obtained by the first stage treatment reaction before adding water.

More precisely, the following methods may be adopted for the suspension after the first stage treatment:

a. adding a predetermined amount of water and a catalyst, then adding a separately prepared metal alkoxide solution dissolved in a polar organic solvent, b. adding a separately prepared aqueous solution of a catalyst and a predetermined amount of water and further separately prepared metal alkoxide solution dissolved in a polar organic solvent separately and simultaneously, and c. adding a predetermined amount of metal alkoxide before adding a catalyst and a predetermined amount of water provided separately.

Among these, the method in which water and the metal alkoxide solution are separately added at the same time when the speed of the hydrolysis reaction is high is preferred in that a state of excessive water during the hydrolysis reaction can thus be avoided.

A high reaction temperature is preferred to increase the speed of the hydrolysis reaction; however, it is appropriately determined in consideration of the boiling point of the polar organic solvent used etc. When operating at a temperature in the vicinity of the boiling point, the solution can be cooled and refluxed by using a condenser.

Thus, the highly anti-corrosive thin-platelet like metal pigments according to the present invention can be obtained by filtering, separating and drying the solid parts of the suspension of a polar organic solvent obtained from the second stage treatment.

The treatment by phosphoric acid compounds or boric acid compounds and the combination of different types of hydrated metal oxides forming the hydrated metal oxide layer are determined in consideration of the transparency of the highly anti-corrosive thin-platelet like metal pigments to be obtained, the amount of light reaching to the thin-platelet like metal substrates beneath the treatment layers, the amount of reflected light depending thereon, the desired coloring properties, etc.; Among about it is preferred to form a layer of hydrated silicon oxides generated by hydrolyzing silicon alkoxide on the surface of thin-platelet like metal substrates treated with phosphoric acid compounds and/or boric acid compounds.

The highly anti-corrosive thin-platelet like metal pigments according to the present invention have good anti-corrosive property and, even when left for 2 hours in a heated hydrochloric aqueous solution with a pH of 1.8, hydrogen gas was rarely generated.

The term "hydrated silicon oxide", as used in the present specification, denotes compounds in which silicon oxides, hydrates of silicon oxides and hydroxyl group bonded silicon oxides and other bonded states are present as an inclusive whole. Similarly, the term "hydrated metal oxides", as used in the present specification including the claims, denotes compounds obtained by drying and, if desired, calcining hydrolyzed metal salts and metal compounds such as metal alkoxide etc., and compounds in which metal oxides, hydrates of metal oxides and hydroxyl group bonded metal and other bonded states are present as an inclusive whole.

The highly anti-corrosive thin-platelet like metal pigments of the present invention are mainly used as pigments having metallic luster particularly having brilliance, for paints, inks, plastics, etc. Since they can be used in aqueous system or a powder system, they are particularly preferred, from the environmental point of view and for improving the work environment, as powder coatings and as water-borne paints and inks. These highly anti-corrosive thin-platelet like metal pigments, depending on their intended use, can be used to carry out e.g. treatments to light resistance, water and weather resistance required for applications as automobile paints (e.g. according to JP (A) Sho. 63-130673, JP (A) Hei. 1-292067, etc.), e.g. treatments for high plane orientation properties (leafing) required in the painting and printing fields (e.g. according to JP (A) 2001-106937, Japanese Patent Application Hei. 11-347084, etc.), water-borne treatments for water-based paints or inks (e.g. according to JP (A) 8-283604, etc.), silicon treatment for improving dispersibility and hydrogenpolysiloxane treatment for improving the hydrophoric and oil phobic properties for applications in the cosmetics field, surface treatments for weld-line prevention when used as resin (e.g. according to JP (A) Hei. 3-100068), and different treatments for improving dispersibility.

The highly anti-corrosive thin-platelet like metal pigments in the present invention are indispensable for and required as base for the novel interference colored pigments having metallic luster according to the present invention described below; and the two treatment stages described above are not merely for imparting high anti-corrosion to the surface of the thin-platelet like metal substrates, they are also important for achieving a dense and homogeneous hydrated metal oxide layer subsequently formed on the upper layer thereof. Namely, only by forming the highly anti-corrosive layer obtained by the treatments described above is it possible to pass to the subsequent hydrated metal oxides coating process by the wet process method and to easily coat hydrated metal oxides on the upper layer of the anti-corrosive layer.

Hereinafter, the interference colored pigments having metallic luster (claims 16-21) of the present invention which are based on the highly anti-corrosive thin-platelet like metal pigments of the present invention and which are obtained by further secondary coating of hydrated metal oxides comprising one or more layers are described. In the present invention, the secondary coating of hydrated metal oxides on the surface of the anti-corrosive thin-platelet like metal can also be formed by the vapor phase method (chemical vapor deposition (CVD) and physical vapor deposition (PVD)) and the sol-gel method; however, it is preferred to use the wet process method which, in contrast to the vapor phase and sol-gel methods, has no limitations with regard to the raw material and production facilities and which is an easy to operate simple process with a wide range of applications.

It is a major characteristic of the present invention that at this stage the so-called wet process method can be adopted because of the excellent anti-corrosive properties.

Metals constituting the secondary coating of hydrated metal oxides for generating interference colors, include not only titanium, aluminum, zirconium, tin, zinc, iron, chromium and cobalt, also include silicon, boron, etc. Hydrated metal oxides of titanium, zirconium, tin, zinc, silicon, boron, etc. having transparency and hydrated metal oxides of iron, chromium, cobalt, etc. having a colored transparency are appropriately selected for use. Among these, titanium is preferred in consideration of its high index of refraction and iron is preferred in consideration of the interference color having its inherent color.

The interference colored pigments having metallic luster of the present invention can be obtained by using water-soluble metal salts with the sol-gel method on their own or in combination (i.e. as hydrated composite metal oxides), in a multilayer coating characterized in that the material is changed for each layer (e.g. in the order of hydrated titanium oxides—hydrated iron oxides, etc.), or in a multilayer coating characterized in that hydrated metal oxide layers with a high refractive index (representative of this type are e.g. hydrated titanium oxides, hydrated zirconium oxides, etc.) alternate with hydrated metal oxide layers with a low refractive index (e.g. hydrated aluminum oxides, hydrated silicon oxides, hydrated boron oxides, etc.), etc.

A definition of the wet process method, as used in the present invention, has been given before, more precisely, the method consists of, in a an aqueous system and (1) In the case of neutralization hydrolysis, selecting the desired water-soluble metal salt (e.g., nitrate salt, sulfate salt, chloride, acetate salt, etc.) and predetermined the prescribed amount of aqueous solution, while separately preparing an alkaline solution, dropping these into a suspension of highly anti-corrosive thin-platelet like metal pigments which is the base obtained beforehand while maintaining a predetermined pH, forming a hydrolyzed layer and, thereafter, washing, filtering, drying and, if desired, calcining;

(2) In the case of thermal hydrolysis, adding the predetermined amount of the desired water-soluble metal salt to a suspension of highly anti-corrosive thin-platelet like metal pigments which is the base obtained beforehand and, by heating, forming a hydrolyzed layer and, thereafter, washing, filtering, drying and, if desired, calcining.

Moreover, as a variation of the method by neutralization hydrolysis (1), a method using, instead of the alkaline aqueous solution, acetoamide and urea producing alkalinity through heating, (the so-called "homogeneous precipitation method") can also be mentioned. Thus, the interference colored pigments having metallic luster, which are the object of the present invention, can be obtained by selecting at optionally water-soluble metal salts, using them on either solely or in combination and by changing the time at which they are introduced to the suspension.

More specifically, the metallic luster interference colored pigments having metallic luster of the present invention can be prepared, in the case of a coating of a single hydrated metal oxide, by selecting one water-soluble metal salt such as titanium, zirconium, tin, zinc, iron, chromium, cobalt, etc. for coating the hydrated metal oxide by means of neutralization hydrolysis under alkaline conditions or by thermal hydrolysis; in the case of a coating of composite metals, by mixing plural metal salts for coating the hydrated composite metal oxides by neutralization hydrolysis or by thermal hydrolysis; or, in the case of a multilayer coating, by sequentially adding the different metal salts for coating sequential layers of hydrated metal oxides; and by, thereafter, washing, filtering, drying and, if desired, calcining. When forming, according to the present invention, a multilayer coating with alternate layers, aqueous solutions of metal salts, forming the relative high refractive index layers (mentioned before) and low refractive index layers (mentioned before), are alternately dropped, in the same way, into the base, i.e. the suspension of highly anti-corrosive thin-platelet like metal pigments, sequentially coating the hydrolates thereof. The color chromaticity of the interference colored pigments having metallic luster obtained by forming an alternate layer multilayer coating is improved through the accumulation of interferences when the reflection/transmission of light at the boundary of each layer is repeated by the alternate coating of plural layers alternately controlling the optical thickness (for details refer to WO 98/53011). The color chromatiaty of the interference colored pigments having metallic luster obtained by forming an alternate layer multilayer coating have a high chromatiaty which cannot be obtained by single hydrated metal oxide coating having high refractive index using a single metal.

In the present invention, if hydrated titanium oxides are included in the constituent elements of the interference color layer, it is possible to change them to rutile-type by using a tin compound or other rutile agents for increasing the refractive index of the hydrated titanium oxide crystals. The coloring properties are improved by the change to a rutile-type titanium oxide.

The interference colored pigments having metallic luster obtained by the present invention produce the so-called color travel effect (characterized in that the observed colors vary with the observation angle), combining the inherent color of the metal (masstone) and the interference colors, because the anti-corrosive layer is homogeneous and dense and the high refractive index hydrated metal oxides coated on the surface thereof have a high homogeneity and denseness.

In these interference color layers, known colored or black inorganic and organic pigments of ultrafine particles can be included to produce interference colored pigments having metallic luster maintaining the inherent colors (masstones) of these pigments while generating interference colors. This has only become possible by adapting the easy to operate wet process method, which makes it possible to extend these pigments to various color ranges and to broaden the range of applications.

By performing different types of additional surface treatments, the metallic luster interference colored pigments having metallic luster obtained according to the present invention meet with the quality required for the applications for which these treatments are used. For example, it is possible to carry out treatments to light resistance, water-and weather resistance required for applications as automobile paints (e.g. according to JP (A) Sho. 63-130673, JP (A) Hei. 1-292067, etc.), e.g. treatments to impart high plural orientation properties (leafing) required in the painting and printing fields (e.g. according to JP (A) 2001-106937, Japanese Patent Application Hei. 11-347084, etc.), water-borne treatments for water-borne paints or inks (e.g. according to JP (A) 8-283604, etc.), silicon treatment for improving dispersibility and hydrogen-polysiloxane treatment for improving hydropholic and oilpholic properties for applications in the cosmetics field, surface treatments for weld-line prevention when used as resin (e.g. according to JP (A) Hei. 3-100068), and different treatments for improving dispersibility.

Hereinafter, the uses of the highly anti-corrosive thin-platelet like metal pigment prepared by the present invention and the interference colored pigments having metallic luster using the same as base will be described. The highly anti-corrosive thin-platelet like metal pigments and the interference colored pigments having metallic luster obtained according to the present invention can be used in various applications such as paints, printing inks, resin compositions, cosmetics, etc. Specific examples thereof will be given below. Although not particularly described, highly anti-corrosive thin-platelet like metal pigments and interference colored pigments having metallic luster according to the present invention used in the following examples include the product prepared by performing the above-mentioned various treatments.

Use for Paints

Examples of use in paints are those of organic solvent-type paints, NAD paints, water-borne paints, emulsion paints, colloidal paints and powder coating. The pigments of the present invention can be mixed in a proportion of 1-100 wt % to the paint resins as solid parts. A proportion of 1-70 wt % is preferred. A proportion of 1-20 wt % is particularly preferable. For improving the dispersibility, the surface of the pigments in the present invention can be treated with a silane coupling agents and a titanium coupling agents. Examples of resin components for the paints in the present invention are acrylate resins, alkyd resins, unsaturated polyester resins, amino resins, melamine resins, polyurethane resins, epoxy resins, polyamide resins, phenol resins, cellulose resins, vinyl resins, silicone resins, fluorine resins, etc. These resins may be used alone or in combination of two or more.

In water-borne paint, resin of an emulsion type containing cross-linking resin by acrylate melamine resins may be exampliefied.

Examples of mixtures and admixtures include combination pigments, organic pigments, inorganic pigments, dripping preventers, viscosity adjusting agents, sedimentation preventers, cross-linking promoters, curing agents, leveling agents, defoaming agents, plasticizers, antiseptic agents, antifungal agents, ultraviolet stabilizers, fillers, etc. Examples of combination pigments are titanium dioxide, calcium carbonate, clay, talc, barium sulfate, white carbon, chromium oxide, zinc oxide, zinc sulfide, zinc powder, metal powder pigments (such as., aluminum flakes, colored aluminum flakes, stainless steel flakes, titanium flakes, etc.), iron black, yellow iron oxide, red iron oxide, chrome yellow, carbon black, molybdate orange, Prussian Blue, ultramarine blue, cadmium type pigments, fluorescent pigments, soluble azo dyes, insoluble azo dye, condensed azo dye, phthalocyanine pigments, condensed polycyclic pigments, composite oxide pigments, graphite, mica (e.g., white mica, gold mica, synthetic mica, fluorine tetra silicon mica, etc.), metal oxide coated mica (such as, titanium oxide coated mica, titanium dioxide coated mica, (hydrated) iron oxide coated mica, mica coated with iron oxides and titanium oxides, mica coated with lower ordered titanium oxides), metal oxide coated graphite (e.g., titanium dioxide coated graphite, etc.), thin-platelet like alumina, metal oxide coated alumina (e.g., dioxide coated alumina, iron oxide coated thin-platelet like alumina, $Fe_2O_3$ coated thin-platelet like alumina, $Fe_3O_4$ coated thin-platelet like alumina, interference color metal oxide coated thin-platelet like alumina, etc.), MIO, metal oxide coated MIO, metal oxide coated silica flakes metal oxide coated alumina, metal oxide coated glass flakes called as optical effect pigments, photochromic pigments, thermochromic pigments, holographic pigments called as functional pigments, etc. By combining these and other pigments, novel hue and chromaticity can be improved. These paints can be applied to wood, plastic, metal sheets, glass, ceramic, paper, film, sheeting, translucent films of reflector for LCDs, etc. Examples of uses for paints include automobiles, buildings, marine vessels, electric household appliances, canned goods, industrial equipment, traffic signs, plastic, household goods, etc.

Examples of the structure of the coated film exemplified e.g. a film coated in the order of a base coat layer, middle coat layer, layer containing the pigments of the present invention and clear layer, and a structure in the order of base coat layer, middle coat layer comprising the pigments of the present invention and clear layer, etc.; however, the structure of the coated film is not limited thereto.

Examples of the method for forming the coated film are one-coat/one-bake, two-coat/one-bake, two-coat/two-bake, three-coat/one-bake, three-coat/two-bake, three-coat/three-bake. Examples of coating methods include electrostatic coating, spray coating, airless coating, roll coating, immersion coating, etc.

Use for Printing Inks

Examples of use in printing inks include relief printing ink, lithographic printing ink, intaglio printing ink, ink for metal plates, radiation curable ink, UV ink, EB ink, flexo ink, screen ink, offset ink, gravure ink, etc. and water-borne ink thereof, etc. The pigments of the present invention can be mixed in a proportion of 1-100 wt % to the resins, as solid parts, in the ink. A proportion of 1-70 wt % is preferred. And a proportion of 1-20 wt % is particularly preferred. Moreover, the surface of the pigments in the present invention can be treated with silane coupling agents and titanium coupling agents, etc. Examples of resin components include e.g. rosin maleic resins, maleic resins, alkyd resins, polyamide resins, phenol resins, petroleum resins, urethane resins, epoxy resins, acrylate resins, butyral resins, melamine resins, epoxy resins, vinyl chloride resins, vinylidene chloride resins, cellulose resins, vinyl resins, unsaturated polyester resins, cellulose resins, etc. These resins may be used alone or in combination of two or more.

Examples of mixtures include combination pigments, organic pigments, inorganic pigments and additives such as varnishes, reducer, compounders, ultra varnishes, gelling agents, drying promoter, antioxidants, preventer for transmission of ink to nack, lubricants, surface active agent, etc. Further example include dripping preventor, viscosity adjusting agent, sedimentation preventors, cross-linking agents, curing agents, leveling agents, defoaming agents, plasticizers, antiseptic agents, antifungal agents, ultraviolet stabilizers, fillers, etc.

Examples of combination pigments are extender pigments; precipitated barium sulfate; precipitated calcium carbonate; alumina white; magnesium carbonate and white carbon; white pigments such as titanium oxide, zinc oxide, etc.; black pigments such as carbon black; yellow pigments such as chrome yellow, disazo yellow, Hansa yellow; red pigments such as brilliant carmine 6B, lake red C, permanent red F5R, Rhodamine Lake, etc.; blue pigments such as phthalocyanine blue, Victoria Blue Lake, Prussian Blue; orange pigments such as chrome vermilion, disazo orange; green pigments such as phthalocyanine green, etc.; violet pigments such as methyl violet lake, dioxazine violet, etc.; other pigments such as isoindolinone, benzimidazoline, condensed azo, quinacdrine, etc.; composite oxide pigments; graphite; mica (e.g., white mica, gold mica, synthetic mica, fluorine tetravalent silicon mica, etc.); metal oxide coated mica (e.g., titanium oxide coated mica, titanium dioxide coated mica, (hydrated) iron oxide coated mica, mica coated with iron oxides and titanium oxides, mica coated with lower order titanium oxides); metal oxide coated graphite (e.g., titanium dioxide coated graphite, etc.); thin-platelet like alumina; metal oxide coated alumina (e.g., dioxide coated alumina., iron oxide coated thin-platelet like alumina, $Fe_2O_3$ coated thin-platelet like alumina, $Fe_3O_4$ coated thin-platelet like alumina, interference color metal oxide coated thin-platelet like alumina, etc.); MIO; metal oxide coated MIO; metal oxide coated silica flakes metal oxide coated alumina; metal oxide coated glass flakes called optical effect pigments; photochromic pigments thermochromic pigments; holographic pigments called functional pigments; etc. These inks can be printed on wood, plastic, metal sheets plato, glass, ceramic, paper, corrugated cardboard, film, sheet canned goods, translucent films of reflection for LCDs, etc. When the pigments of the present invention in combined with these pigments new hue and colors are appeared. Especially the pigments according to the present invention are suitable for preventing the counterfeiting of securities, tickets, passenger tickets, etc., due to their color travel effect (the hue changes depending on the reviewing angle).

Moreover, when used in printing inks, it is particularly preferred to perform a high plane orientation treatment (mentioned above) on the interference colored pigments having a metallic luster obtained according to the present invention. Pigments subjected to such a surface treatment can be mixed with various kinds of printing inks and used for offset printing, gravure printing, screen printing, ultraviolet cure printing, and relief and lithographic printing. The use of pigments which have been subject to a high plane orientation treatment as an inks particularly results in improvement of coloration of interference color on printed surface and color travel effect by changing the viewing angle caused thereby and that is prepared for printing for preventing he counterfeiting.

Use for Plastics

In the present invention, when incorporated in plastics, the pigments can be mixed with the resin either directly or after previously making into pellets and then making into various molded products by means of extrusion molding, calender molding, blow molding, etc. As to the resin component, polyolefin-based thermoplastic resins as well as epoxy-based, polyester-based and polyamide (nylon)-based thermoplastic resins can be used. A small amount of pigments can be sufficient to effectively produce the color effects of the interference colored pigments with metallic luster of the present invention, e.g., when forming a multiple layer plastic bottle, the external appearance of the bottle can be made to appear effectively by incorporating the pigments in the resin of the outer layer. Especially pigments obtained according to the present invention on which an additional orientation plane treatment has been performed are preferred in that they have good coloring properties. Naturally, it is possible to use metallic luster interference colored pigments related to the present invention on which a weld-line prevention treatment (e.g., encapsulation, etc.) has been performed. The highly anti-corrosive thin-platelet like metal pigments and the interference colored pigments having metallic luster obtained according to the present invention can also be used in combination with other pigments. Examples of pigments that can be used in combination with the pigments of the present invention include titanium dioxide, calcium carbonate, clay, talc, barium sulfate, white carbon, chromium oxide, zinc oxide, zinc sulfide, zinc powder, metal powder pigments, iron black, yellow iron oxide, red iron oxide, chrome yellow, carbon black, molybdate orange, Prussian Blue, ultramarine Blue, cadmium type pigments, fluorescent pigments, soluble azo dyes, insoluble azo dyes, condensed azo dyes, phthalocyanine pigments, condensed polycyclic pigments, composite oxide pigments, graphite, mica (e.g., white mica, gold mica, synthetic mica, fluorine tetravalent silicon mica, etc.), metal oxide coated mica (such as, titanium oxide coated mica, titanium dioxide coated mica, (hydrated) iron oxide coated mica, mica coated with iron oxides and titanium oxides, mica coated with lower ordered titanium oxides), metal oxide coated graphite (e.g., titanium dioxide coated graphite, etc.), thin-platelet like alumina, metal oxide coated alumina (e.g., dioxide coated alumina, iron oxide coated thin-platelet like alumina, $Fe_2O_3$ coated thin-platelet like alumina, $Fe_3O_4$ coated thin-platelet like alumina, interference color metal oxide coated thin-platelet like alumina, etc.), MIO, metal oxide coated MIO, metal oxide coated silica flakes metal oxide coated alumina, metal oxide coated glass flakes called optical effect pigments, photochromic pigments, thermochromic pigments, holographic pigments called functional pigments, etc.

Use for Cosmetics

Examples of use in cosmetics include make-up, hair care products, cosmetic packs, etc. E.g., the pigments can be used in gel, lipstick, foundation (including emulsion, liquid, oil-type emulsions, etc.), cheek rouge, mascara, nail enamel, eyebrow pencil, eye shadow, eyeliner, hair products, etc. They can be used in a proportion of 1-100 wt %. E.g., for foundations 1-50 wt %, for eye shadow 1-80 wt %, for lipstick 1-40 wt %, for nail enamel 0.1-20 wt % can be mentioned.

Examples of mixed components will be given below. Examples of combination pigments include titanium dioxide, calcium carbonate, clay, talc, barium sulfate, white carbon, chromium oxide, zinc oxide, zinc sulfide, zinc powder, metal powder pigments, iron black, yellow iron oxide, red iron oxide, chrome yellow, carbon black, molybdate orange, Prussian Blue, ultramarine blue, cadmium type pigments, fluorescent pigments, soluble azo dyes, insoluble azo dyes, condensed azo dyes, phthalocyanine pigments, condensed polycyclic pigments, composite oxide pigments, graphite, mica (e.g., white mica, gold mica, synthetic mica, fluorine tetravalent silicon mica, etc.), metal oxide coated mica (e.g., titanium oxide coated mica, titanium dioxide coated mica, (hydrated) iron oxide coated mica, mica coated with iron oxides and titanium oxides, mica coated with lower ordered titanium oxides), metal oxide coated graphite (e.g., titanium dioxide coated graphite, etc.), thin-platelet like alumina, metal oxide coated alumina (e.g., titanium dioxide coated alumina, iron oxide coated thin-platelet like alumina, $Fe_2O_3$ coated thin-platelet like alumina, $Fe_3O_4$ coated thin-platelet like alumina, interference color metal oxide coated thin-platelet like alumina, etc.), MIO, metal oxide coated MIO, metal oxide coated silica flakes metal oxide coated alumina, metal oxide coated glass flakes called optical effect pigments, photochromic pigments thermochromic pigments, holographic pigments called functional pigments, sericite, magnesium carbonate, silica, zeolite, hydroxyapatite, chromium oxide, cobalt titanate, glass beads, nylon beads, silicone beads, etc.

Examples of organic pigments include red nos. 2, 3, 102, 104, 105, 106, 201, 202, 203, 204, 205, 206, 207, 208, 213, 214, 215, 218, 219, 220, 221, 223, 225, 226, 227, 228, 230-1, 230-2, 231, 232, 405; yellow nos. 4, 5, 201, 202-1, 202-2, 203, 204, 205, 401, 402, 403, 404, 405, 406, 407; green nos. 3, 201, 202, 204, 205, 401, 402; blue nos. 1, 2, 201, 202, 203, 204, 205, 403, 404; orange nos. 201, 203, 204, 205, 206, 207, 401, 402, 403; brown no. 201; violet nos. 201, 401; black no. 401.

Examples of natural colors include salol yellow, carmine, β-carotin, hibiscus color, capsaicin, carminic acid, laccaic acid, gurcumin, riboflavin, shikonin, etc. Further, examples of other components include fats and oils, waxes, surfactants, oxidation inhibitors, UV absorbers, vitamins, hormones, squalanes, liquid paraffins, palmitic acids, stearic acids, bees wax, hydrocarbons of myristyl myristate etc., acetone, toluene, butyl acetate, solvents of acetic esters etc., antioxidants, antiseptic agents, polyhydric alcohols, perfumes, etc. By combining the pigments of the present invention with these pigments and components, novel effect colors and functions can be found.

When used in cosmetics, the pigments according to the present invention can be used e.g. in compact cakes, in cream, in lipstick, etc.; however, they are particularly effective when used in make-up, characterized in that colors are particularly important. Naturally, it is possible to use interference colored pigments having metallic luster related to the present invention on which a surface treatment (mentioned before) has been performed.

Other Uses

The pigments of the present invention can be used by combining with color toners for copying machines etc. E.g., when it is used as s color toner for copying machines, a color travel effect is achieved thereby an effect of preventing the counterfeiting can be achieved.

EXAMPLES

Hereinafter, the present invention is for then described in more detail by reference to the Examples and comparative Examples, which however are not to intend to limit the present invention.

Example 1

Preparation of Highly Anti-corrosive Thin-platelet like Metal Pigments 1-a) Treatment with a Phosphoric Acid Compound: SS5588 (P)

1 g of phosphoric acid (85%) was added to a suspension in which 78.2 g of an aluminum paste sample {Sparkle Silver SS5588 (manufactured by Silberline, effective components: 64%, D50: about 18 μm)} were dispersed in 500 ml acetone, and stirred for 30 minutes at room temperature. Thereafter, the suspension was filtered and washed with acetone, this operation was repeated once; and then, the solid parts were filtered and the thin-platelet like metal treated with phosphoric acid compound (SS5588(P)) was obtained. The SS5588 (P) obtained among the sample for the following coating.

1-b) Hydrated Silicon Oxide Coating: $SiO_2$/SS5588(P)

In a round bottom flask equipped with a reflux condenser and an agitator, the thin-platelet like metal, treated with phosphoric acid compound, obtained in step 1-a) (SS5588(P)) was suspended in 750 ml of ethanol. The suspension was heated to 65° C. after 200 g of water and 20 g of a 28% aqueous ammonia solution had been added. Next, a solution of 60 g of tetraethoxysilane diluted with 76 ml of ethanol was added to it small amounts while stirring. This reaction mixture was stirred for 20 hours at 65° C., then filtered from the mother liquid, washed with ethanol and dried, the highly anti-corrosive platelet like metal pigments ($SiO_2$/SS5588(P)) were obtained.

Example 2

Preparation of Highly Anti-corrosive Thin-platelet like Metal Pigments 2-a) Treatment with a Phosphoric Acid Compound: 550N(P)

5 g of monoisodecyl acid phosphoric acid was added to a suspension in which 76 g of an aluminum paste sample {550N (manufactured by Showa Aluminum Co., Ltd., effective components 65.8%, D50: about 19 μm)} were dispersed in 500 ml of acetone and stirred for 30 minutes at room temperature. Thereafter, the suspension was filtered and washed with acetone, this operation was repeated once; and then, the solid parts were filtered and the thin-platelet like metal treated with phosphoric acid compound (550N(P)) was obtained. The 550N (P) obtained among the sample for the following coating.

2-b) Hydrated Silicon Oxide Coating: $SiO_2/550N(P)$

In a round bottom flask equipped with a reflux condenser and an agitator, the aluminum treated with phosphoric acid compound, obtained in step 2-a) (550N(P)) was suspended in 750 ml of ethanol. The suspension was heated to 65° C. after 200 g of water and 20 g of a 28% aqueous ammonia solution had been added. Next, a solution of 60 g of tetraethoxysilane diluted with 76 ml of ethanol was added to it while stirring. This reaction mixture was stirred for 20 hours at 65° C., then filtered from the mother liquid, washed with ethanol and dried, the highly anti-corrosive thin-platelet like metal pigments ($SiO_2/550N(P)$) were obtained.

Example 3

Preparation of Highly Anti-corrosive Thin-platelet like Metal Pigments 3-a) Treatment with a Phosphoric Acid Compound: SL800(P)

5 g of monoisodecyl acid phosphoric acid was added to a suspension in which 66.3 g of aluminum paste sample {SL800 (manufactured by Showa Aluminum Co., Ltd., effective components 75.4%, D50: about 18 µm)} were dispersed in 500 ml of acetone and stirred for 30 minutes at room temperature. Thereafter, the suspension was filtered and washed with acetone, this operation was repeated once; and then, the solid parts were filtered and the thin-platelet like metal treated with phosphoric acid compound (SL800 (P)) was obtained. The SL800(P) obtained among the sample for the following coating.

3-b) Hydrated Silicon Oxide Coating: $SiO_2$/ SL800(P)

In a round bottom flask equipped with a reflux condenser and an agitator, the aluminum treated with phosphoric acid compound, obtained in step 3-a) (SL800 (P)) was suspended in 750 ml of ethanol. The suspension was heated to 65° C. after 200 g of water and 20 g of a 28% aqueous ammonia solution had been added. Next, a solution of 60 g of tetraethoxysilane diluted in 76 ml of ethanol was added to it while stirring. This reaction mixture was stirred for 18 hours at 65° C., then filtered from the mother liquid, washed with ethanol and dried, the highly anti-corrosive platelet like metal pigments ($SiO_2$/SL800 (P)) were obtained.

Example 4

Preparation of Highly Anti-corrosive Thin-platelet like Metal Pigments 4-a) Treatment with a Phosphoric Acid Compound: 5422NS (P)

1 g of phosphoric acid (85%) was added to a suspension in which 66.4 g of aluminum paste sample {5422NS (manufactured by Toyo Aluminum Co., Ltd., effective components 75.3%, D50: about 20 µm)} were dispersed in 500 ml of acetone and stirred for 30 minutes at room temperature; thereafter, the suspension was filtered and washed with acetone, this operation was repeated once; and then, the solid parts were filtered and the thin-platelet like metal treated with phosphoric acid compound (5422NS (P)) was obtained. The 5422NS(P) obtained among the sample for the following coating.

4-b) Hydrated Silicon Oxide Coating: $SiO_2$/5422NS(P)

In a round bottom flask equipped with a reflux condenser and an agitator, the aluminum treated with phosphoric acid compound, obtained in step 4-a) (5422NS (P)), was suspended in 750 ml of ethanol. The suspension was heated to 65° C. after 200 g of water and 20 g of 28% aqueous ammonia solution had been added. Next, a solution of 60 g of tetraethoxysilane and 2 g of γ-(2-aminoethyl)aminopropyltrimethoxysilane diluted with 76 ml of ethanol was added to it while stirring. This reaction mixture was stirred for 18 hours at 65° C., then filtered from the mother liquid, washed with ethanol and dried, the highly anti-corrosive platelet like metal pigments ($SiO_2$/5422NS (P)) were obtained.

Example 5

Preparation of Highly Anti-corrosive Thin-platelet like Metal Pigments 5-a) Treatment with a Boric Acid Compound: 5422NS(B)

0.3 g of boric acid was added to a suspension in which 66.4 g of an aluminum paste sample {5422NS (manufactured by Toyo Aluminum Co., Ltd., effective components 75.3%, D50: about 20 µm)} were dispersed in 500 ml of acetone, and stirred for 30 minutes at room temperature; thereafter, the suspension was filtered and washed with acetone, this operation was repeated; Thereafter, the solid parts were filtered and the thin-platelet like metal treated with boric acid compound (5422NS(B)) was obtained. The 5422NS(B) obtained among the sample for the following coating.

5-b) Hydrated Silicon Oxide Coating: $SiO_2$/5422NS(B)

In a round bottom flask equipped with a reflux condenser and an agitator, the aluminum with a boric acid compound obtained in step 5-a) (5422NS(B)) was suspended in 750 ml of ethanol. The suspension was heated to 65° C. after 200 g of water and 20 g of 28% aqueous ammonia solution had been added. Next, a solution of 60 g of tetraethoxysilane and 2 g of γ-(2-aminoethyl)-aminopropyltrimethoxysilane diluted with 76 ml of ethanol was added to it while stirring. This reaction mixture was stirred for 18 hours at 65° C., then filtered from the mother liquid, washed with ethanol and dried, the highly anti-corrosive thin-platelet like metal pigments ($SiO_2$/ 5422NS (B)) were obtained.

Example 6

Preparation of the Interference Colored Pigments having Metallic Luster: $TiO_2/SiO_2$/5422NS(P)

50 g of the highly anti-corrosive thin-platelet like metal pigments $SiO_2$/5422NS(P) obtained in Example 4-b) were suspended in 1 liter of water and heated to 75° C. under stirring. 50.6 g of $SnCl_4.5H_2O$ solution ($SnCl_4.5H_2O$, 29 g/liter) were dropped to this suspension while beeping PH at 1.8 using sodium hydroxide of 32 wt %. Next, titanium tetrachloride solution ($TiCl_4$, 448 g/liter) was dropped into the suspension while keeping the pH at 1.8 using sodium hydroxide of 32 wt %. The reaction was finished until at the green color was reached. From the suspension, the solid parts were filtered, washed with water, then dried and calcined, the interference colored pigments having metallic luster ($TiO_2/SiO_2$/ 5422NS(P)) were obtained. It was confirmed by X-ray diffraction that the hydrated titanium layer of the coating was a rutile type. 1 weight part of this powder was dispersed in 9 weight parts of an acryl-modified nitrocellulose lacquer and coated on a black and white paper with an applicator (bar coater #20). The hue change (color travel effect) depended on viewing angle was appeared from the measurement using the goniospectrophotometer GCMS-3 (manufactured by Murakami Color Research Laboratory). The results of the color measurement is shown in Table 1.

TABLE 1

Result of color measurement by goniospectrophotometer

| Incident angle/ observation angle | Luster (L*) | a* | b* | Chromaticity | Hue angle |
|---|---|---|---|---|---|
| 45/0  | 47.07  | 3.05   | −11.82 | 12.21 | 284.47 |
| 45/10 | 62.64  | 0.76   | −6.58  | 6.63  | 276.63 |
| 45/20 | 90.40  | −3.34  | 2.78   | 4.34  | 140.21 |
| 45/30 | 132.64 | −8.73  | 15.32  | 17.63 | 119.67 |
| 45/40 | 177.62 | −13.28 | 24.60  | 27.96 | 118.37 |
| 45/50 | 182.69 | −13.51 | 23.92  | 27.47 | 119.47 |
| 45/60 | 143.38 | −10.18 | 17.57  | 20.31 | 120.09 |
| 45/70 | 102.65 | −4.73  | 9.86   | 10.93 | 115.63 |

Notes:
The chromaticity represents the root value of $a^{*2} + b^{*2}$.
The hue angle represents $\tan^{-1}(b^*/a^*)$.

From the result of the table, when angle of color variation was changed, hue changes were observed in such a way to the state from the chromaticity 27.96 at 45/40 and hue angle of 118° (greenish yellow) to the chromaticity of 12.21 at 45/0 and hue angle of 284° (reddish blue), whereby a color travel effect was confirmed.

Comparative Example 1

Preparation of SiO$_2$/5422NS 66.4 g of the aluminum paste {5422NS (manufactured by Toyo Aluminum Co., Ltd., effective components 75.3%, D50: about 20 μm)} were dispersed in 500 ml of acetone, the suspension was stirred for 30 minutes at room temperature, then filtered, washed with acetone, and this operation was repeated once; and thereafter, the solid parts were obtained by filtering. In a round bottom flask equipped with a reflux condenser and an agitator, the solid parts were suspended in 750 ml of ethanol. The suspension was heated to 65° C. after 200 g of water and 20 g of a 28% aqueous ammonia water solution had been added. Next, a solution of 60 g of tetraethoxysilane diluted with 76 ml of ethanol was added to it while stirring. This reaction mixture was stirred for 18 hours at 65° C., then filtered from the mother liquid, washed with ethanol and dried, and SiO$_2$/5422NS was obtained Comparative Example 2

Preparation of TiO$_2$/SiO$_2$/5422NS 50 g of the hydrated silicon oxide coated SiO$_2$/5422NS powder obtained in Comparative Example 1 was suspended in 1 liter of water and heated to 75° C. under stirring. 50.6 g of SnCl$_4$.5H$_2$O solution (SnCl$_4$.5H$_2$O, 29 g/liter) were dropped into this suspension while keeping pH at 1.8 using sodium hydroxide of 32 wt %. Next, titanium tetrachloride solution (TiCl$_4$, 448 g/liter) was dropped into the suspension obtained while keeping pH at 1.8 using sodium hydroxide of 32 wt %. The reaction was finished until green color was reached. The solid parts were filtered from the suspension, washed with water dried and calcined. The interference colored pigments having metallic luster TiO$_2$/SiO$_2$/5422NS was obtained. It was confirmed by X-ray diffraction that the hydrated titanium oxide in the coated layer was a rutile type. 1 weight part of this powder was dispersed in 9 weight parts of an acryl-modified nitrocellulose lacquer and coated on a black and white paper with an applicator (bar coater #20). Result of the color measurement using a goniorespectrophotometer GCMS-3 (manufactured by Murakami Color Research Laboratory) are shown in Table 2.

TABLE 2

Result of color measurement by goniorespectrophotometer

| Incident angle/ observation angle | Luster (L*) | a* | b* | Chromaticity | Hue angle |
|---|---|---|---|---|---|
| 45/0  | 46.35  | −1.20 | 3.64  | 3.83  | 108.27 |
| 45/10 | 64.43  | −3.43 | 9.17  | 9.79  | 110.52 |
| 45/20 | 89.49  | −5.69 | 15.15 | 16.19 | 110.56 |
| 45/30 | 123.62 | −8.38 | 21.75 | 23.31 | 111.06 |
| 45/40 | 164.98 | −8.38 | 25.02 | 26.39 | 108.50 |
| 45/50 | 167.99 | −7.99 | 21.96 | 23.36 | 109.99 |
| 45/60 | 124.47 | −6.40 | 17.54 | 18.67 | 110.03 |
| 45/70 | 91.50  | −3.41 | 13.30 | 13.73 | 104.40 |

Notes:
The chromaticity represents the root value of $a^{*2} + b^{*2}$.
The hue angle represents $\tan^{-1}(b^*/a^*)$.

From the result of the table, when the maximum chromaticity at 45/40 and hue angle 109° (greenish yellow) was 26.39, even when angle of vation was changed, the change in hue angle was narrow (from 104° to 111° (greenish yellow)), whereby no color travel effect was observed.

Anti-corrosion Test (Measurement of the Amount of Generated Hydrogen Gas):

1 g of each sample was dispersed in 100 g of warm water (75° C.) of pH of 1.8 adjusted by hydrochloric acid (HCl), and the temperature of this suspension was kept at 75° C. under stirring. After predetermined each time, the amount of generated hydrogen (H$_2$) from the suspension was measured. Measurements were taken during 120 minutes. A comparison between untreated Al flakes (the surface treatment agent was removed by washing), Al flakes (P) {treated with phosphoric acid compounds only (first stage treatment)}, and SiO$_2$/Al flakes (P) {coated with hydrated silicon oxide after being treated with phosphoric acid compounds (first stage treatment+second stage coating)} is shown in FIG. 3, 1-4. Similar comparison among Al-flakes treated by boric acid compounds (Example 5) instead of by phosphoric acid compounds in shown in FIG. 5.

FIG. 1 shows a comparison of the amount of generated hydrogen gas in the case of use of SS5588 among the untreated SS5588, SS5588(P) and SiO$_2$/SS5588(P).

Here, SS5588(P) was obtained in 1-a) of Example 1 and SiO$_2$/SS5588(P) was obtained in Example 1-b) of Example 1. An amount of generated hydrogen gas was very little for SiO$_2$/SS5588(P) according to the present invention.

Figure 2:
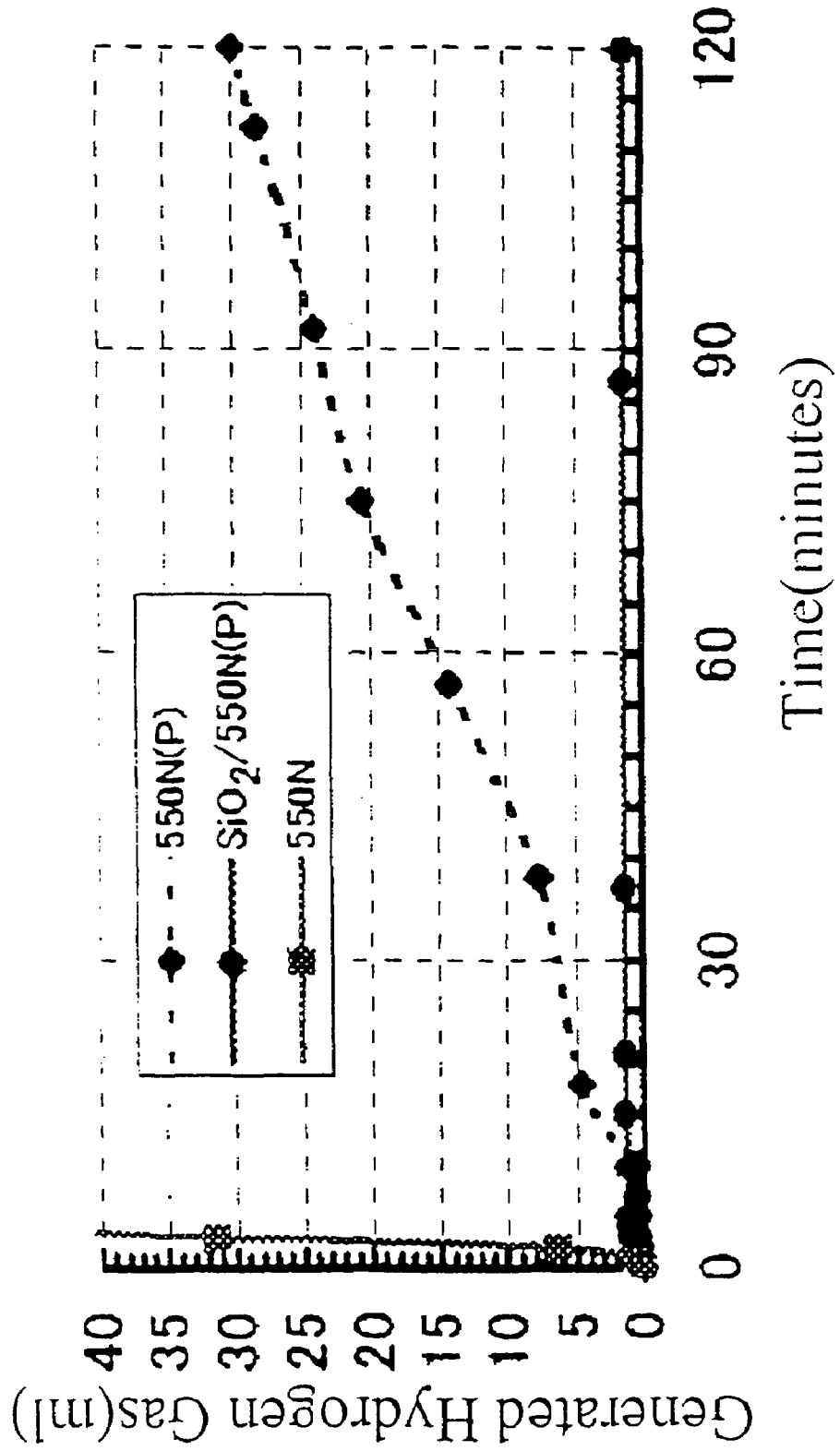
FIG. 2 shows a comparison of the amount of hydrogen gas in the case of use of 550N was used among the untreated 550N, 550N(P) and $SiO_2$/550N(P).

FIG. 2 shows a comparison of the amount of generated hydrogen gas in the case of use of 550N among the untreated 550N, 550N(P) and SiO$_2$/550N(P).

Here, 550N(P) was obtained in 2-a) of Example 2 and SiO$_2$/550N(P) was obtained in 2-b) of Example 2. No hydrogen gas was generated with the SiO$_2$/550N(P) according to the present invention.

Figure 3:
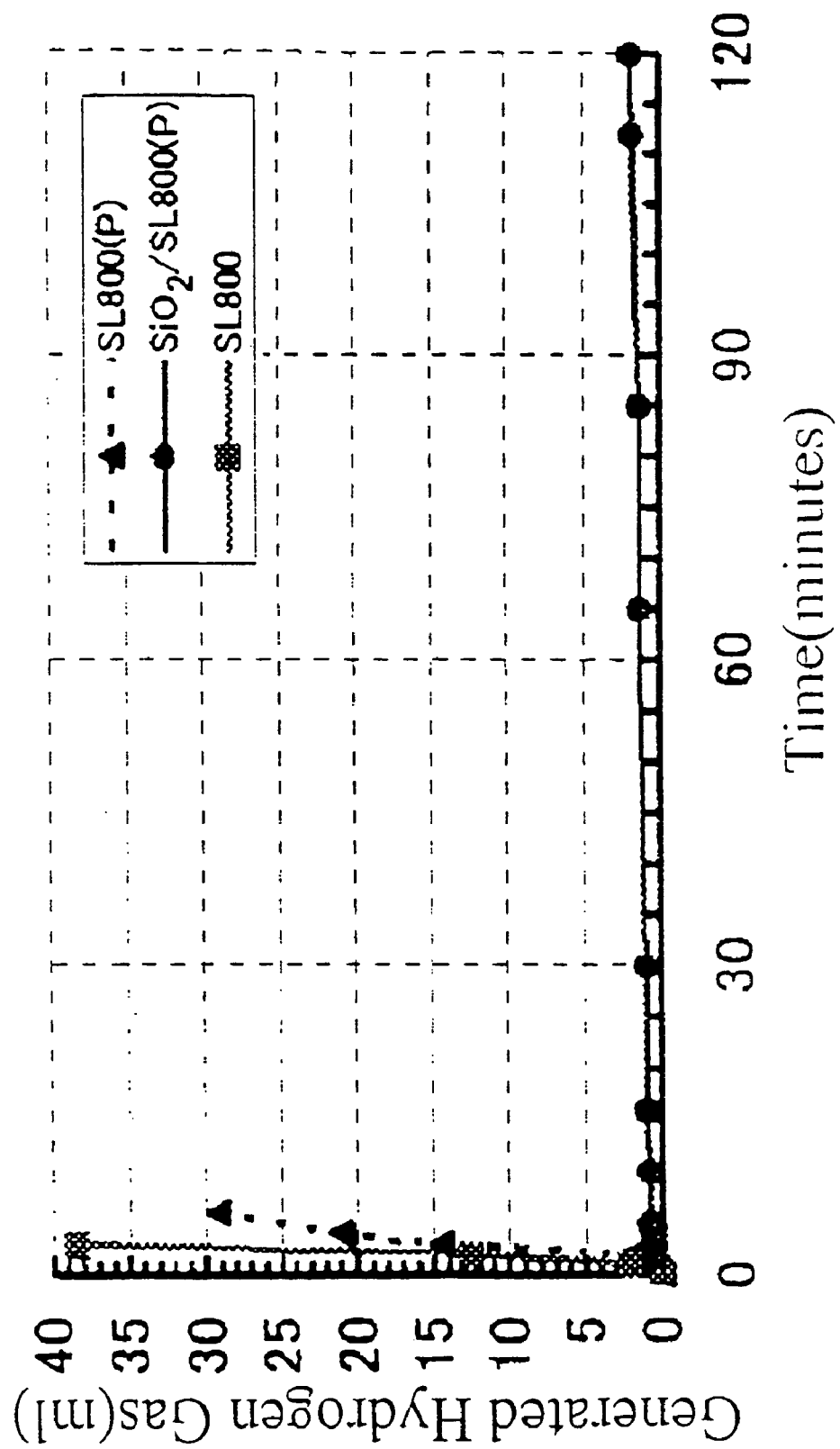
FIG. 3 shows a comparison of the amount of hydrogen gas in the case of use of SL800 was used among the untreated SL800, SL800(P) and $SiO_2$/SL800(P).

FIG. 3 shows a comparison of the amount of generated hydrogen gas in the case of use of SL800 among the untreated SL800, SL800(P) and SiO$_2$/SL800(P).

Here, SL800(P) was obtained in 3-a) of Example 3 and SiO$_2$/SL800(P) was obtained in 3-b) of Example 3. Hydrogen gas was rarely generated with the SiO$_2$/SL800(P) according to the present invention.

Figure 4:
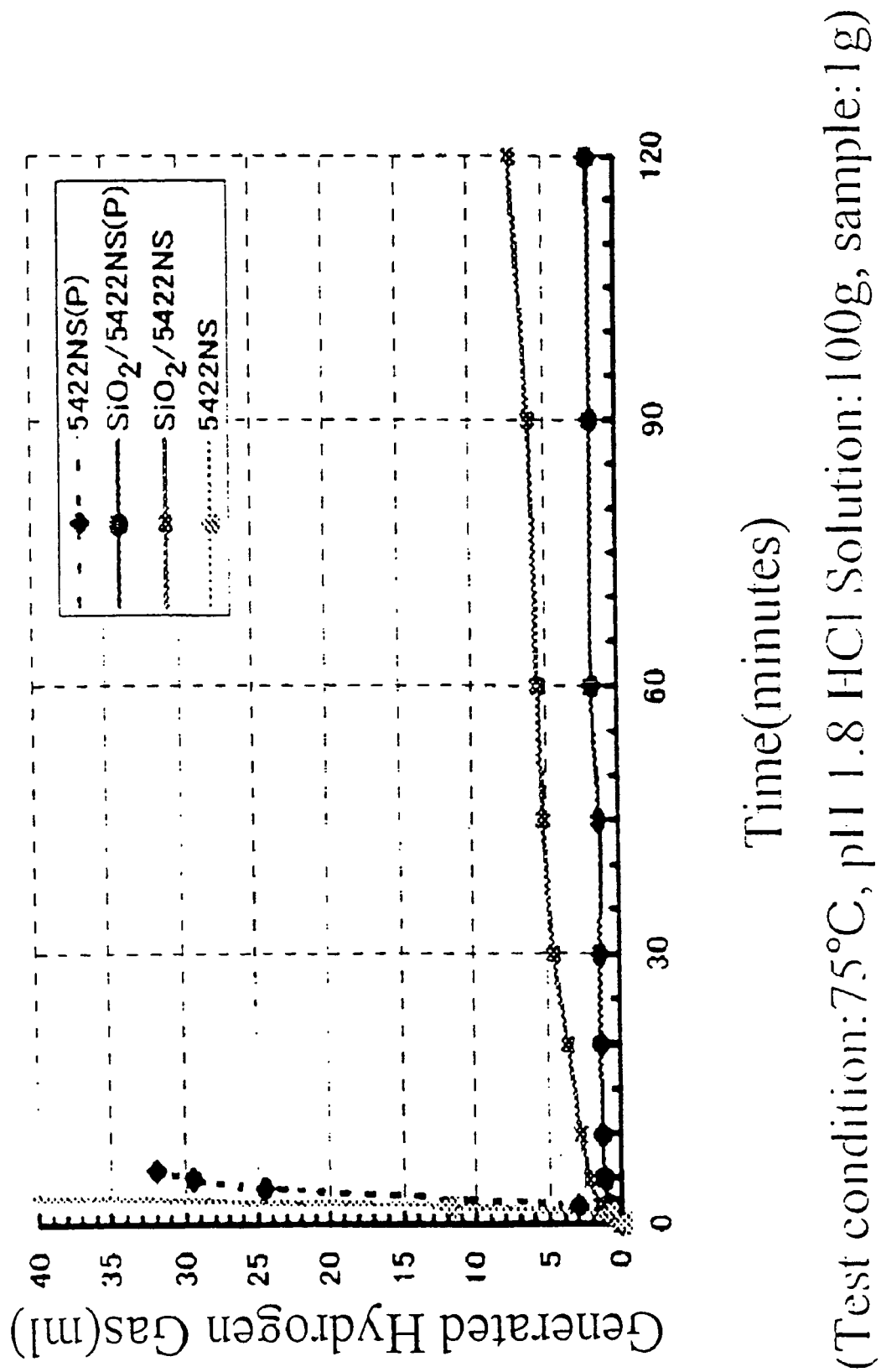
FIG. 4 shows a comparison of the amount of hydrogen gas in the case of use of 5422NS was used among the untreated 5422NS, 5422NS(P), $SiO_2$/5422NS(P) and $SiO_2$/5422NS.

FIG. 4 shows a comparison of the amount of generated hydrogen gas in the case of use of 5422NS among the untreated 5422NS, 5422NS(P), SiO$_2$/5422NS(P) and SiO$_2$/5422NS.

5422NS(P) was obtained in 4-a) of Example 4, SiO$_2$/5422NS(P) was obtained in 4-b) of Example 4 and SiO$_2$/5422NS was obtained in Comparative Example 1 (flakes treated only by the second stage coating, i.e. the "hydrated silicon oxide coating", without subject to the first stage treatment, i.e. the "phosphoric acid compound treatment"). Hydrogen gas was rarely generated with the SiO$_2$/5422NS(P) flakes according to the present invention. As for 5422 NS(P) treated only with a large amount of hydrogen gas was generated within a short period of time, phosphoric acid compound (the first stage treatment) and much hydrogen gas was also generated for the SiO$_2$/5422NS after the time lapsed.

FIG. 5 shows a comparison of the amount of generated hydrogen gas in the case of use of 5422NS among the untreated 5422NS, 5422NS(B), SiO$_2$/5422NS(B) and SiO$_2$/5422NS.

Here, 5422NS(B) was obtained in 5-a) of Example 5, SiO$_2$/5422NS(B) was obtained in 5-b) of Example 5 and SiO$_2$/5422NS was obtained in Comparative Example 1 (flakes treated only by the second stage coating, i.e. the "hydrated silicon oxide coating", without subject to the first stage treatment, i.e. the "boric acid compound treatment"). Hydrogen gas was rarely generated with the SiO$_2$/5422NS(B) according to the present invention. As for 5422 NS(B) treated only with boric acid compound (first stage treatment), a large amount of hydrogen gas was rarely generated within a short period of time and, much hydrogen gas was also generated with the SiO$_2$/5422NS after the time lapsed.

Measurement of the Specific Surface Area

The specific surface area was measured with a fully-automated gas adsorption analyzer (Autosorb 6 manufactured by QuantaChrome). The results are shown in Table 3.

(Table 3)

TABLE 3

Measurement of the specific surface area

| Sample | Specific surface area A(m$^2$/g) |
|---|---|
| Untreated 5422NS | 2.24 |
| SiO$_2$/5422NS(P) (Example 4-b) | 3.01 |
| SiO$_2$/5422NS (Comparative Example 1) | 8.32 |

It was demonstrated in table 3 the two stage treatment where a treatment with a phosphoric acid compounds and a hydrated silicon oxide coating were combined according to the present invention gave less increase in the specific surface area, namely, the coated layer was dense and smooth as compared with comparative Examples. It was further demonstrated in FIG. 4 that the product according to said two stages treatments showed better anti-corrosive property as compared with the case of a coated layer with hydrated silicon oxide only.

Dispersibility Evaluation

The dispersibility was evaluated by means of the hiding power. The more hiding power, the higher dispersibility is. Hiding power was calculated in such a way that 1 weight part of the samples was dispersed in 9 weight parts of an acryl-modified nitrocellulose lacquer and coated on a black and white paper with an applicator (bar coater #20), the reflectance of the samples was measured using a color meter (CR-300 manufactured by Minolta Camera Co., Ltd.) and the hiding power was calculated by the formula below. The results are shown in Table 4.

Hiding power=100×(Diffuse reflectance of coated film on Blackground 45°/0°)/(Diffuse reflectance of coated film on white ground 45°/0°)

(Table 4)

TABLE 4

Hiding power

| Sample | Hiding power (%) |
|---|---|
| 5422NS | 99.6 |
| SiO$_2$/5422NS(P) (Example 4-b) | 96.5 |
| SiO$_2$/5422NS (Comparative Example 1) | 79.1 |

It was demonstrated by the above results that the highly anti-corrosive thin-platelet like metal pigments according to the present invention, where thin-platelet like metal substrate were treated with phosphoric acid compound combined with hydrated silicon oxide coating layer on the surface thereof, is consisted of dense coated layers due to small specific surface area, and had a high dispersibility, due to high hiding power.

Specific examples for the use will now be shown as hereafter.

Use Example 1

Use Examples for Paint
Paint based on pearlescent pigments:

(Composition A)

| Acrydick 47-712 | 70 weight parts |
|---|---|
| Super Beckamine G821-60 | 30 weight parts |

(Composition B)

| Samples of Examples 1-6 | 10 weight parts |
|---|---|
| Pearlescent pigments | 10 weight parts |

(Composition C)

| Ethyl acetate | 50 weight parts |
|---|---|
| Toluene | 30 weight parts |
| n-butanol | 10 weight parts |
| Solvesso #150 | 40 weight parts |

100 weight parts of Composition A were mixed with 20 weight parts of Composition B and then diluted with Ford Cup #4 for a viscosity of 12-15 seconds suitable for spray-coating with Composition C, whereupon a basecoat was formed by spray coating.

Clear paint:

| Acrydic 44-179 | 14 weight parts |
|---|---|
| Super Beckamine L117-60 | 6 weight parts |
| Toluene | 4 weight parts |
| Methyl isobutyl ketone (MIBK) | 4 weight parts |
| Butyl cellosolve | 3 weight parts |

This composition was coated on the above pearlescent coating, dried at 40° C. for 30 minutes, air-dried at room temperature and baked at 130° C. for 30 minutes.

It was confirmed that the paint films formed with compositions containing samples of Examples 1-5 had a good metallic luster and that the paint film formed with the composition containing a sample of Example 6 had a high brightness, had a high chromaticity and a color trevel effect.

Use Example 2

Use Example for Plastic

| | |
|---|---|
| High density polyethylene (pellets) | 100 weight parts |
| Samples of Examples 1-6 | 1 weight part |
| Magnesium stearate | 0.1 weight parts |
| Zinc stearate | 0.1 weight parts |

These components were dry-blended and formed by injection molding.

It was confirmed that the moldings containing samples of Examples 1-5 had a good metallic luster and that the molding containing a sample of Example 6 had high brightness, high chromaticity and a color travel effect.

Use Example 3

Use Example for Ink

| | |
|---|---|
| CCST medium (nitrocellulose resin) | 10 weight parts |
| Samples of Examples 1-6 | 8 weight parts |

The solvent NC 102 was added to the ink composition blended from the above components, and the ink was prepared with a viscosity of 20 seconds with Zahn Cup No. 3.

It was confirmed that the prints obtained with inks containing samples of Examples 1-5 had a good metallic luster and that the print obtained with an ink containing a sample of Example 6 had high brightness, high chromaticity and a color travel effect.

Use Example 4

Use Example for Cosmetics

Use example for compact powder:

| | |
|---|---|
| Talc | 50 weight parts |
| Samples of Examples 1-6 | 25 weight parts |
| Color pigments | 5 weight parts |
| Isopropyl myristate | a suitable amount |
| Magnesium stearate | 2 weight parts |

Use example for a foundation:

| | |
|---|---|
| Talc | 38 weight parts |
| Samples of Examples 1-6 | 25 weight parts |
| Mica (8 μm) | 10 weight parts |
| Magnesium stearate | 3 weight parts |
| Nylon powder 12 | 8 weight parts |

-continued

| | |
|---|---|
| Yellow iron oxide | 1.9 weight parts |
| Red iron oxide | 0.8 weight parts |
| Titanium oxide | 1.0 weight part |
| Mineral oil | a suitable amount |
| (caprylic acid, capric acid) triglyceride | 3.3 weight parts |
| Butylparaben | 0.1 weight parts | what is claimed is:

1. A highly anti-corrosive thin platelet-like metal pigment comprising thin-platelet shaped metal substrates treated with boric acid compounds or phosphoric acid compounds and boric acid compounds, and thereon one or more layers containing one or more hydrated metal oxides of one or more metals selected from the group consisting of silicon, aluminum, zirconium, titanium and tin, whereby said treatment and said layers result in a passivated substrate.

2. The highly anti-corrosive thin platelet-shaped metal pigments according to claim 1, wherein the thin-platelet shaped metal substrates are metallic pigments having metallic luster.

3. The highly anti-corrosive thin-platelet shaped metal pigments according to claim 2, wherein the metallic pigments having metallic luster is any one of aluminum flakes, titanium flakes, gold flakes, silver flakes, copper-zinc alloy flakes, stainless steel flakes or bronze flakes.

4. The highly anti-corrosive thin-platelet shaped metal pigments according to claim 1, wherein the hydrated metal oxides are hydrated silicon oxides.

5. The highly anti-corrosive thin-platelet shaped metal pigments according to claim 1, wherein the hydrated metal oxides are prepared by the sol-gel method.

6. The highly anti-corrosive thin-platelet shaped metal pigments according to claim 5, wherein the sol-gel method is performed by hydrolysis of metal alkoxide.

7. The highly anti-corrosive thin-platelet shaped metal pigments according to claim 6, wherein the hydrolysis of metal alkoxide is performed by using a basic catalyst.

8. The highly anti-corrosive thin-platelet shaped metal pigments according to claim 1, wherein the amount of boric acid compounds, or phosphoric acid compounds and boric acid compounds, is 0.0001-0.1 g as $B_2O_3$ or $P_2O_5$ and $B_2O_3$ per unit surface area ($m^2$) of thin-platelet shaped metal substrates and the amount of metal compounds used for preparing a hydrated metal oxide coated layer, is 0.01-1.0 g as $SiO_2$, $Al_2O_3$, $ZrO_2$, $TiO_2$ and $SnO_2$ per unit surface area ($m^2$) of thin-platelet shaped metal substrates.

9. A preparing method of preparing highly anti-corrosive thin platelet-like metal pigments, comprising dispersing a thin-platelet shaped metal substrate in a polar organic solvent, and
1) adding phosphoric acid compounds and/or boric acid compounds thereto stirring it, and accordingly treating the substrate,
2) preparing a layer of a hydrated metal oxide on the surface of said substrates by sol-gel methods, whereby from (1) and (2) said substrate is passivated.

10. The method according to claim 9, wherein the sol-gel method is performed by hydrolysis of a metal alkoxide solution that is dissolved in a polar organic solvent.

11. The method according to claim 9, wherein the metal composing the coated layer of hydrated metal oxide are one or more metals selected from the group consisting of silicon, aluminum, tin, zirconium and titanium.

12. The preparing method according to claim 10, wherein the metal alkoxide solution is added after adding of water and a catalyst.

13. The preparing method according to claim 10, wherein the metal alkoxide solution is added at the same time as an aqueous solution containing a catalyst.

14. The preparing method according to claim 10, wherein the aqueous solution containing a catalyst is added after addition of the metal alkoxide solution.

15. The production method according to claim 12, wherein the catalyst is a basic catalyst.

16. A highly anti-corrosive thin-platelet shaped metal pigment comprising, on the surface of thin-platelet shaped metal substrates treated with boric acid compounds or phosphoric acid compounds and boric acid compounds, one or more layers containing one or more hydrated metal oxides of one or more metals selected from the group consisting of silicon, aluminum, zirconium, titanium and tin, whereby from said treatment and said layer said substrate is passivated, and further coated with a secondary hydrated metal oxide layer comprising one or more layers, whereby an interference pigment results.

17. The pigments according to claim 16, wherein the secondary coated layer of hydrated metal oxides is prepared a wet process method, a chemical vapor deposition process method or a physical vapor deposition process method.

18. The pigments according to claim 17, wherein the secondary coated layer of hydrated metal oxides is prepared by a wet process method.

19. The pigments according to claim 16, wherein the secondary coated layer of hydrated metal oxides is the coated layers containing one or more hydrated metal oxides of one or more metals selected from the group consisting of titanium, aluminum, zirconium, tin, zinc, iron, chromium, cobalt, silicon and boron.

20. The pigments according to claim 16, wherein the secondary coated layers of hydrated metal oxides are multi-coated layer having different hydrated metal oxides.

21. The pigments according to claim 20, wherein the secondary coated layers of hydrated metal oxides are alternately multi-coated layers of hydrated metal oxides having a high refractive index and having a low refractive index.

22. A method of preparing highly anti-corrosive thin platelet-like metal pigments according to claim 1, comprising dispersing a thin-platelet-shaped metal substrate in a polar organic solvent, and 1) adding phosphoric acid compounds and/or boric acid compounds thereto, stirring it, and accordingly treating the substrate,
2) preparing a layer of a hydrated metal oxide on the surface of said substrates by sol-gel methods, whereby from (1) and (2) the substrate is passivated.

23. A process according to claim 9, wherein (1) is conducted at room temperature.

24. A highly anti-corrosive thin platelet-like metal pigment comprising thin-platelet shaped aluminum flake substrates treated with boric acid compounds or phosphoric acid compounds and boric acid compounds, and thereon one or more layers containing one or more hydrated metal oxides of one or more metals selected from the group consisting of silicon, aluminum, zirconium, titanium and tin, whereby said treatment and said layers result in a passivated substrate.

25. A highly anti-conosive thin platelet-like metal pigment consisting of thin-platelet shaped metal substrates treated with boric acid compounds or phosphoric acid compounds and boric acid compounds, and thereon one or more layers of one or more hydrated metal oxides of silicon, aluminum, zirconium, titanium and tin, whereby said treatment and said layers result in a passivated substrate.

* * * * *